US005624675A

United States Patent [19]
Kelly

[11] Patent Number: 5,624,675
[45] Date of Patent: *Apr. 29, 1997

[54] GENITAL LUBRICANTS CONTAINING ZINC SALTS TO REDUCE RISK OF HIV INFECTION

[76] Inventor: Patrick D. Kelly, 33 Berry Oaks, St. Louis, Mo. 63122

[*] Notice: The term of this patent shall not extend beyond the expiration date of Pat. No. 5,482,053.

[21] Appl. No.: 150,870

[22] Filed: Nov. 12, 1993

Related U.S. Application Data

[63] Continuation-in-part of Ser. No. 816,278, Jan. 3, 1992, abandoned, which is a continuation-in-part of Ser. No. 737,169, Jul. 29, 1991, Pat. No. 5,208,031, which is a continuation-in-part of Ser. No. 528,495, May 25, 1990, abandoned, which is a continuation-in-part of Ser. No. 362,058, Jun. 6, 1989, abandoned.

[51] Int. Cl.$^6$ .................................. A01M 25/04
[52] U.S. Cl. .................. 424/405; 424/409; 424/642; 424/430; 424/436; 523/122; 514/557; 514/934; 514/967; 514/969
[58] Field of Search .................... 424/405, 67, 430, 424/436, 444, 642; 523/122; 514/934, 967, 969, 557

[56] References Cited

U.S. PATENT DOCUMENTS

| | | | |
|---|---|---|---|
| 2,584,166 | 2/1952 | Stevenson et al. | 424/430 |
| 3,235,445 | 2/1966 | Judge et al. | 424/67 |
| 4,384,003 | 5/1983 | Kazmirooki et al. | 424/341 |
| 4,407,818 | 10/1983 | Lionelle et al. | 424/145 |
| 4,410,517 | 10/1983 | Stillman | 424/195 |
| 4,465,666 | 8/1984 | Lukas et al. | 424/289 |
| 4,548,950 | 10/1985 | Baxendale et al. | 514/510 |
| 4,604,404 | 8/1986 | Munson et al. | 514/494 |
| 4,938,969 | 7/1990 | Schinitsky et al. | 424/642 |
| 4,996,048 | 2/1991 | Bhagwat et al. | 424/80 |
| 5,208,031 | 5/1993 | Kelly | 424/412 |
| 5,232,691 | 8/1993 | Lemole | 424/78.02 |

FOREIGN PATENT DOCUMENTS

| | | | |
|---|---|---|---|
| 1146859 | 5/1983 | Canada | 424/642 |
| 8402845 | 8/1984 | WIPO | 424/642 |
| WO87/02246 | 10/1987 | WIPO | |

OTHER PUBLICATIONS

Brawner, T.A., et al, "A Combined Chemical–Physical Treatment for Herpes Simplex Lesions in Guinea Pigs," *Arch. Dermatol. Res.* 265: 71–77 (1979).

(List continued on next page.)

*Primary Examiner*—Neil S. Levy
*Attorney, Agent, or Firm*—Patrick D. Kelly

[57] ABSTRACT

A method is disclosed for using a topical genital lubricant with a non-toxic, non-irritating zinc salt during sexual intercourse. The lubricant is spread upon one or more genital surfaces to create an anti-viral chemical barrier that reduces the risk of infection by the human immunodeficiency virus (HIV), the virus that causes AIDS. Suitable zinc salts include zinc acetate, zinc propionate, and other non-irritating water-soluble organic zinc salts that dissociate readily. When dissolved in water, these salts release divalent zinc ions ($Zn^{++}$), which apparently can reduce HIV infectivity by at least three mechanisms. First, zinc ions form crosslinking bonds with cysteine and histidine residues in proteins (such as the gp120 protein of HIV), thereby "gluing" HIV particles to each other, to proteins in vaginal fluids, and to dead or dying cells that will soon be sloughed off from the genital surfaces. This reduces the ability of the HIV to infect susceptible cells. Second, zinc is the active agent in diaper rash ointments and calamine lotion, and it promotes healing and closure of lesions, microabrasions, and other skin breaches; this reduces the ability of HIV to penetrate the skin and reach lymphocytes. Third, concentrations of zinc that do not harm skin can kill HIV-infected lymphocytes, thereby preventing the lymphocytes from infecting other cells via cell—cell binding mechanisms. The toxicity of zinc to lymphocytes also explains why the anti-HIV activity of zinc was not recognized previously, in standard lymphocyte assays.

3 Claims, 2 Drawing Sheets

OTHER PUBLICATIONS

Brody, I., "Topical treatment of recurrent herpes simplex . . . zinc sulphate solution," *Brit. J. Dermatol.* 104: 191–194 (1981).

Eby, G.A., and W.W. Halcomb, "Use of topical zinc to prevent recurrent herpes simplex infection: review of literature and suggested protocols," *Medical Hypotheses* 17: 157–165 (1985).

Fahim, M., et al, "New Treatment for Herpes Simplex Virus Type 2 [Ultrasound and Zinc, Urea, and Tannic Acid Ointment] Part 1—Male Patients, " *J. Medicine* 9(3): 245–264 (1978).

Fahim, M., et al, "New Treatment for Herpes Simplex Virus Type 2. Part 2—Female Patients," *J. Medicine* 11(2&3): 143–167 (1980).

Fahim, M.S. and Brawner, T.A., "Treatment of Genital Herpes Simplex Virus in Male Patients," *Arch. Andrology* 4: 79–85 (1980).

Tennican, P.O., et al, "The Diverse Effects of Topical and Systemic Administration of Zinc on the Virulence of Herpes Simplex Genitalis," *Life Sciences* 24: 1877–1884 (1979).

Tennican, P. et al, "Topical Zinc in the Treatment of Mice Infected Intravaginally with Herpes Genitalis Virus," *Proc. Soc. Exp. Biol. Med.* 164: 593–597 (1980).

Wahba, A. "Topical Application of Zinc Solutions: A New Treatment for Herpes Simplex Infections of the Skin?" *Acta Derm. Venerol. (Stockholm)* 60: 175–177.

Fitzherbert, J.C., "Genital Herpes and Zinc," *Med. J. Australia*, May 5,1979, p. 399.

Fridlender, B., et al., "Selective inhibition of herpes simplex virus type 1 DNA polymerase by zinc ions," *Virology* 84: 551–554 (1978).

Gordon, Y.J., et al, "Irreversible inhibition of herpes simplex virus replication in BSC–1 cells by zinc ions," *Antimicrob. Agents Chemother.* 8:377–380 (1975).

Gupta, P., and Rapp, F., "Effect of zinc ions on synthesis of herpes simplex virus type 2–induced polypeptides," *Proc. Soc. Exp. Biol. Med.* 152: 455–458 (1979).

Jones, R., "Genital Herpes and Zinc," *Med. J. Australia*, Apr. 7, 1979, p. 286.

Shlomai, J., et al, "Effect of zinc ions on the synthesis of herpes simplex virus DNA in infected BSC–1 cells," *Virology* 66: 330–335 (1975).

Sergio, W. "Zinc Salts that may be Effective Against the AIDS Virus HIV," *Medical Hypotheses* 26(4) : 251–253 (1988).

Chvapil et al, "Reaction of vaginal tissue of rabbit and cheek pouch of hamster to inserted collagen sponges treated with either zinc or copper," *Am. J. Obstet. Gynecol.* 130: 63–70 (1978).

Chvapil et al, "Prelimnary testing of the contraceptive collagen sponge," *Obstet. and Gynecol.* 56: 503–506 (1980).

W.L. Williams, "New antifertility agents active in the rabbit vaginal contraception method," *Contraception* 22: 659–672 (1980).

Zhang et al, "Zinc inhibition of renin and the protease from HIV–1," *Biochemistry* 30; 8717–8721 (1991).

Agren, M.S., "Studies on zinc in wound healing," *Acta Dermato–Venereology, Supplement* 154: 1–36 (1990).

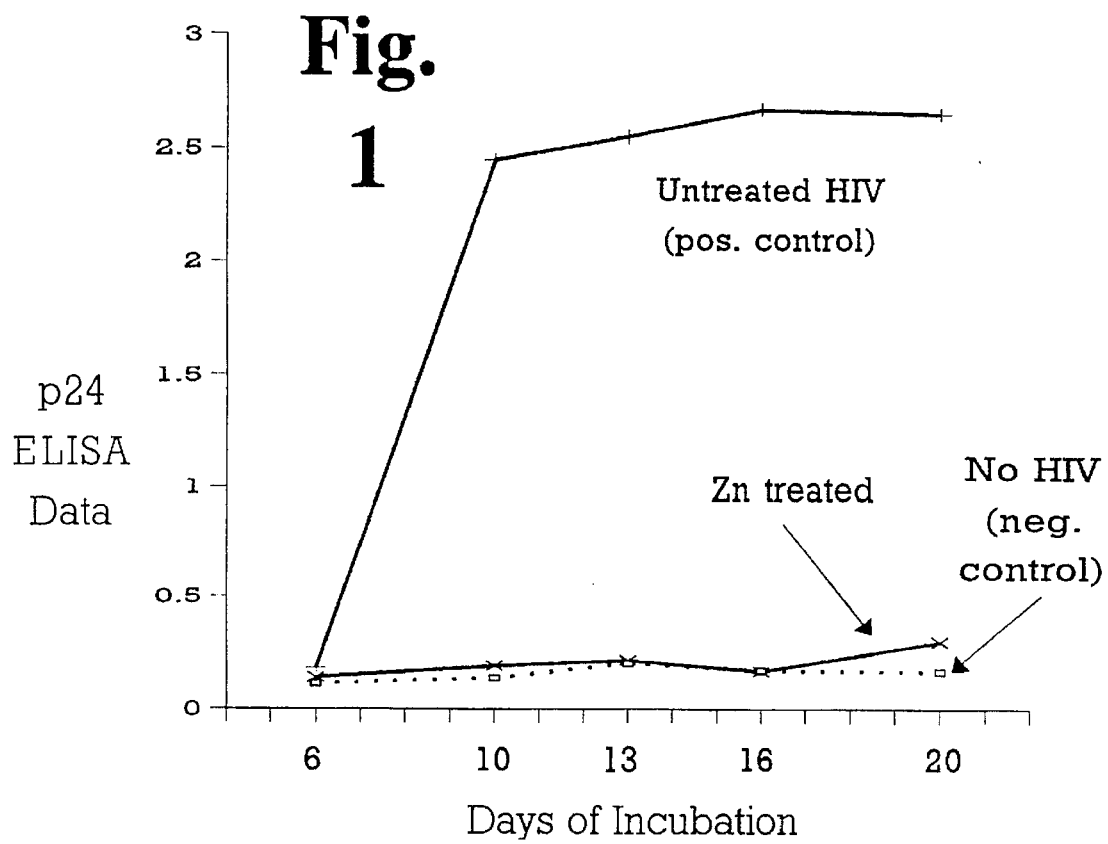
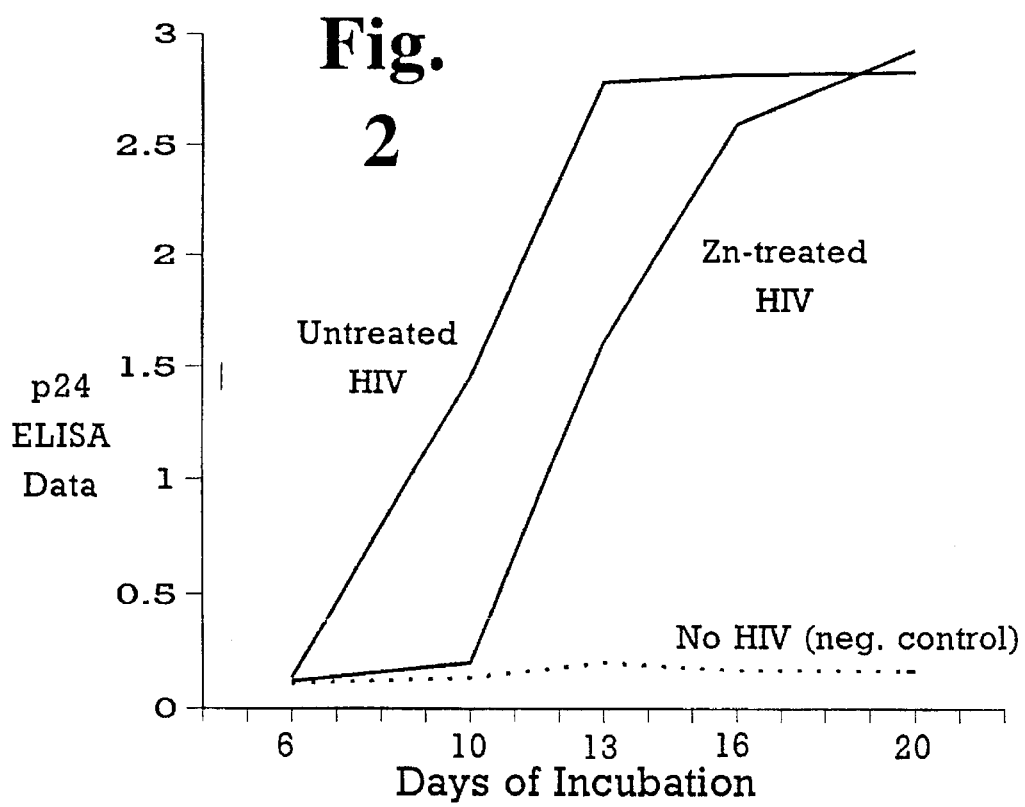

GENITAL LUBRICANTS CONTAINING ZINC SALTS TO REDUCE RISK OF HIV INFECTION

This is a continuation-in-part of U.S. application Ser. No. 07/816,278, now abandoned filed on Jan. 3, 1992, which was a continuation-in-part of U.S. application Ser. No. 737,169, filed on Jul. 29, 1991, which issued as U.S. Pat. No. 5,208,031 on May 4, 1993. That application was a continuation-in-part of U.S. application Ser. No. 528,495, filed on May 25, 1990, now abandoned, which was a continuation-in-part of U.S. application Ser. No. 362,058, filed on Jun. 6, 1989, also abandoned.

BACKGROUND OF THE INVENTION

This invention is in the fields of biochemistry, pharmacology, and anti-viral agents.

There is a major need for improved methods and agents to prevent the spread of acquired immunodeficiency syndrome (AIDS), which is caused by a virus known in America as the human immunodeficiency virus (HIV). Even though the last letter in "HIV" stands for "virus", it is often called the HIV virus, for convenience. It is also called the AIDS virus, and some reports (especially those published prior to 1988) call it the lymphadenopathy virus (LAV) or the HTLV-III virus, which were the names originally used by the research groups in France and the U.S. that isolated it. There are two major strains of the HIV virus, usually designated as HIV-1 and HIV-2.

An excellent introduction to the AIDS epidemic and the HIV virus, with outstanding illustrations and photographs, is provided in the October 1988 issue of *Scientific American*, which was entirely devoted to AIDS. Books that contain detailed information with citations to thousands of scientific and medical articles include Gottlieb et al 1989, Cohen et al 1990, Putney and Bolognesi 1990, and Levy 1989.

Briefly, the HIV virus contains an outer spherical envelope made of a lipid bilayer membrane. Directly inside the outer envelope is a second sphere comprising a protein called p17. All HIV structural proteins (p17, p24, gp41, and gp120) are named after their molecular weight in kilodaltons.

A glycosylated protein called gp41 is embedded in the lipid envelope. A second glycosylated protein called gp120 is non-covalently coupled to the gp41 protein and extends outward from the spherical envelope. Based on electron micrographs, several dozen copies of the gp120 protein appear to be coupled to each HIV particle.

The gp120 protein binds to a human protein designated as CD4 (sometimes referred to as the T4 protein, since it is encoded by a gene known as the T4 gene). The binding reaction is a non-covalent reaction of a type that is often called affinity binding; similar affinity binding reactions occur between antibodies and antigens. The CD4 protein appears on the surfaces of certain types of T-lymphocytes, and in lesser quantities on the surfaces of certain other cells, including monocytes that give rise to white blood cells known as macrophages, glial cells in the brain, and chromaffin cells in the intestine. The binding reaction between the viral gp120 protein and the cellular CD4 protein is very tight; this allows the viral particle to attach itself securely to cells that have the CD4 protein on their surfaces. The cellular entry process may also involve a human protein called CD26, which apparently interacts with a loop of the gp120 protein that becomes exposed after the gp120 protein binds to the CD4 protein.

The viral genes can enter a human cell by any of several processes (Weber and Weiss 1988). In one process, the lipid membrane of the virus fuses with the cell membrane, which is also a lipid bilayer. In an alternate process, an attached virus might be taken into a cell by a process called receptor-mediated endocytosis, in which the viral particle is transported into the cell in a lipid sac that is digested after it enters the cell. In another reported mechanism, in which cells that do not have CD4 receptors can be infected, HIV-infected lymphocytes bind to epithelial cells and inject HIV particles directly into the epithelial cells (Phillips and Bourinbaiar 1992; Pearce-Pratt and Phillips 1993; Zacharopoulos et al 1992). These tests utilized epithelial cells from the intestine, presumably to model the transmission of HIV after anal intercourse, which deposits infected lymphocytes in the colon. The viral assays in those reports were performed seven days after the infection reaction; however, by the time an epithelial cell reaches the surface of a mucous membrane inside the vagina of a woman of reproductive age, the cell remains there only about 96 hours (4 days) before being sloughed off (Averette et al 1970; Ferenczy and Guralnick 1979). That time period is even lower if the woman is taking estrogen. In addition, even though epithelial cells retain their nuclei as they reach a mucous membranes surface (in contrast to epidermal cells, which lose their nuclei before reaching the surface), epithelial nuclei become "pyknotic" (i.e., they become compacted and inactive, in a manner resembling the nuclei of dead or dying cells) as the cells reach an epithelial surface. For both of these reasons, most epithelial cells that have reached a surface layer inside a vagina probably cannot be used by HIV to establish an active reservoir of cells that can support viral replication. It should also be noted that none of the reports co-authored by Phillips and his coworkers evaluated the effects of zinc on the cell—cell binding processes they studied, even though zinc is present in high concentrations in semen and significantly alters the behavior of cell membranes.

The core of an HIV particle contains a protein shell with a conical shape, made of p24 protein units. Unlike most viruses that are enclosed within protein capsids, the p24 protein shell usually is not referred to as a capsid, apparently because the p24 shell is not an enclosed structure (it is open at one end) or because it is surrounded by an outer envelope.

The p24 shell contains two identical strands of single-stranded RNA roughly 9.7 kilobases (kb) long each, and several viral enzymes. One such enzyme carried in the core is reverse transcriptase (RT). When released from the viral core after the virus has entered a cell's cytoplasm or nucleus, the DNA polymerase domain of the RT enzyme uses the viral RNA as a template to synthesize a first strand of DNA. In the next step, an RNase domain of the RT enzyme (which may be an independent polypeptide) digests the viral RNA strand to get it out of the way. In the third step, the viral DNA polymerase synthesizes a second strand of DNA, using the first DNA strand as a template. These three steps generate double-stranded DNA (dsDNA) carrying the viral sequence.

After dsDNA synthesis, a second viral enzyme called integrase (which also is apparently carried inside the viral capsid) helps the viral dsDNA become integrated (i.e., inserted by means of stable covalent bonding) into a chromosome of the cell. The viral dsDNA, when inserted into the chromosome, is called a provirus; some articles apparently also refer to viral dsDNA in free, non-integrated form as a provirus as well.

Inside the nucleus, the proviral dsDNA can remain in an inactive (dormant or latent) state for very long periods. If and when the virus becomes active, the viral genes are transcribed into RNA, primarily by normal cellular enzymes with additional involvement by several viral regulatory genes including tat, rev, and nef.

Some of the viral RNA functions as messenger RNA (mRNA); it is translated into polypeptides by the cell's ribosomes. A viral protease enzyme, which apparently is carried inside the viral core, cleaves the viral polypeptides in a specific manner, releasing functional viral proteins from the longer precursor polypeptides. The viral proteins, along with viral RNA and lipids, are assembled into new viral particles which are released by the cell. Some types of cells release newly generated HIV viruses when the cells lyse (i.e., when the cells are broken apart); other cell lines release HIV by means of a budding process that does not kill the cells.

Zinc Studies by Prior Researchers

A great deal of study and countless proposals have been devoted to potential ways to treat HIV infection, and every known step in the process of infection or replication has been proposed as a target for intervention by drugs that might be able to stop or slow down the virus. Some of those prior efforts and proposals briefly focused on various zinc compounds; however, none of the zinc studies in the prior art encountered any success in the assays used by those researchers, so those researchers lost interest in zinc compounds and turned their attention to other candidates.

For example, when the Applicant submitted samples of several zinc salts (including zinc acetate and zinc gluconate) to the National Cancer Institute for evaluation in a standardized screening test against the HIV virus, the scientists in charge of the NCI's screening program returned the sample without even opening it. The NCI's letter of response, dated Aug. 8, 1991, stated as follows: "After careful consideration, we have decided not to test your zinc salts in our AIDS-antiviral assay . . . We have tested 36 zinc-containing compounds in our in vitro AIDS screen, including zinc gluconate (test results of this inactive compound, NSC 619899, are enclosed . . . ). None of these materials has demonstrated any activity worth pursuing . . . Based on these results, we don't believe that your compounds will show activity in our assay." This is an authoritative statement that, based on their chosen assays, researchers skilled in the art of HIV research did not believe that zinc salts could serve as effective agents against HIV infection.

After analyzing the details of the assay protocols used by other researchers, and after studying the toxicological aspects of zinc when unnaturally high concentrations contact lymphocytes, the Applicant recognized why assays carried out by other researchers did not reveal any substantial beneficial effects of zinc. Briefly, the assays used by the National Cancer Institute evaluated zinc as an agent in the bloodstream; they did not make any effort to evaluate zinc as a topical agent on genital surfaces during intercourse. The assays, described in Weislow et al 1989, involve combining lymphocyte cells, HIV particles, and a candidate antiviral agent simultaneously, then determining whether the antiviral agent protected the lymphocytes.

Such assays may be effective in studying agents that enter the blood and act as viricides or site-specific receptor blockers, but such assays could not identify the antiviral activity of topical agents that do not penetrate the skin or enter the bloodstream. This is especially true in the case of zinc. Zinc concentration in the blood is tightly regulated by a number of proteins and cellular mechanisms (as discussed below), and higher concentrations which do not naturally occur in the blood are relatively toxic to such lymphocytes.

Therefore, assays such as the ones described in Weislow et al 1989 or Resnick et al 1990 did not (and could not) adequately evaluate or identify the antiviral properties of zinc applied topically in a lubricant rather than used as an injected or oral drug.

To overcome those problems, the Applicant developed a two-stage assay that attempts to model what would occur inside the vaginal cavity, but outside the skin, after sexual intercourse between an HIV-positive person and an uninfected partner. These assays use zinc concentrations that can be tolerated on the genital surfaces without irritation or toxicity, even though such concentrations would be toxic to lymphocytes if injected into the blood. During the initial incubation step, which is relatively brief, the zinc is given an opportunity to react with viral particles, with no lymphocytes present. Subsequently, the zinc-virus mixture is diluted to reduce the zinc concentration to levels that are not toxic to lymphocytes, and lymphocytes are then added and incubated with the zinc and virus for 20 days or more. During this second stage of incubation, zinc-treated viruses were shown to be non-infective, while viruses diluted in an identical manner remained highly infective. Those two-stage incubation tests are discussed in more detail below, under the description of the invention.

The following sections provide additional data on zinc toxicology, and on zinc's ability to stabilize membranes and promote the healing of skin deficits.

Zinc Physiology and Toxicology

Zinc is an essential mineral, found in every form of life on earth. Indeed, because of its role as an essential component of certain proteins that interact with DNA, it is believed to be present in every single cell on earth.

In mammals, the great majority of zinc in the body is in skeletal muscle and bone. Blood zinc constitutes less than 0.5% of total zinc in the body, and that fraction is mostly contained inside blood cells or is bound to cell surfaces. In blood plasma, which contains about 1 microgram (ug) of zinc per gram of blood, zinc is bound to various proteins, including albumin, alpha macroglobulin, and transferrin (Vallee 1988; Cousins 1989). These binding reactions are reversible, and they establish an equilibrium between ionic and protein-bound zinc. High zinc levels also stimulate the expression of metallothionein, which tightly chelates zinc (Sadhu and Gedamu 1990). In addition, secretions from the kidneys and pancreas, which are stimulated if zinc levels begin to rise, cause the excess zinc to be excreted in the urine and feces. All of these factors allow the concentration of zinc in blood to be tightly regulated and constrained within a narrow range even though zinc intake can vary widely.

Due to these factors, the toxicity of zinc inside the body is very low. Toxicity problems can arise in unusual situations; for example, inhalation of zinc fumes by metalworkers can lead to a condition called metal fume fever, and genetic defects render certain people unable to metabolize zinc properly. However, such problems are rare, and in healthy people, toxicity caused by excessive zinc is virtually nonexistent and most of the scientific and medical literature on zinc toxicity actually relates to zinc deficiencies, rather than excess zinc.

As stated in Vallee and Falchuk 1993, an extensive review article, "unlike other metals, including those of the IIB series, zinc is virtually nontoxic. The homeostatic mechanisms that regulate its entry into, distribution in, and excretion from cells and tissues are so efficient that no disorders are known to be associated with its excessive accumulation, in contrast to iron, copper, mercury, and other metals.

Second, its physical and chemical properties, including its generally stable association with macromolecules and its coordination flexibility, make it highly adaptable to meeting the needs of proteins and enzymes that carry out diverse biological functions. These and yet other chemical properties form the basis for the extensive participation of zinc in protein, nucleic acid, carbohydrate, and lipid metabolism, as well as in the control of gene transcription and other fundamental biological processes."

Other review articles reach similar conclusions; for example, Leonard et al 1986 concludes that "Toxicity of zinc is low . . . zinc is not mutagenic and has little, if any clastogenic properties . . . zinc is not teratogenic; it can, in fact, avert teratogenicity of other agents. Conversely, zinc deficiency may be harmful." Other toxicologic and physiologic reports include Mills 1989, Calesnick and Dinan 1988, Fosmire 1990, and Bach 1981.

In healthy men, zinc is present in semen at concentrations of 100 to 500 ug/g, and in prostate fluid at concentrations up to 1000 ug/g (Eliasson and Lindholmer 1971; Fair et al 1976; Homonnai et al 1978; Marmar et al 1980). These levels are extraordinarily high compared to blood concentrations of only about 1 ug/ml. In prostate fluid, zinc exerts an antimicrobial effects, to combat infection of a fluid that cannot be directly protected by the immune system (Fair et al 1976). In undiluted semen, zinc suppresses the respiratory activity and motility of sperm cells (Eliasson 1971; Paz et al 1977). Apparently, this allows the sperm cells to stay in a quiescent state, storing and conserving their energy until it is needed. After ejaculation, the zinc is diluted by the female's vaginal fluids and it binds to proteins and other cells inside the vagina. This decreases the concentration of sperm-bound zinc; this, in turn, allows the respiratory activity and motility of the sperm to increase.

Some researchers refer to zinc as a "heavy metal" (e.g., Hedberg et al 1991). This nomenclature uses an arbitrary classification that refers to any element heavier than iron (molecular weight of 56) as a "heavy metal." However, since the phrase "heavy metal" implies "toxic and dangerous" to many readers, zinc (with a molecular weight of 65, close to that of iron) should be regarded as a transition metal or an essential mineral, comparable to iron or manganese.

Membrane Stabilization and Skin Healing Properties

Zinc is widely used as a soothing and healing agent in numerous types of ointments, creams, powders, and other formulations that are applied topically (i.e., spread upon a skin surface). When applied to skin incisions in scientifically controlled studies, it promoted epidermal cell growth and healing (Agren 1990). Zinc is the main active ingredient in ointments used to treat diaper rash (such as Desitin™ baby ointment, sold by Pfizer) and decubitis ulcers (bedsores), in calamine lotion, and in numerous sunblocking creams, antiperspirants, and antifungal agents. Parents have been spreading zinc onto the genitals of their babies for decades, to cure diaper rash; this is strong evidence of its complete absence of toxicity, and of its soothing and healing properties even when applied to highly sensitive areas and to areas that are irritated, inflamed, and in need of soothing.

Some topical formulations contain more than 30% elemental zinc by weight. Most topical formulations use zinc oxide, which gradually solubilizes and releases free zinc ions when it contacts body fluids (Agren 1990).

On a molecular and cellular level, zinc stabilizes and protects cell membranes by mechanisms such as protecting sulfhydryl groups against oxidation and inhibiting the formation of free radicals that randomly attack and degrade membrane-forming lipids and other biomolecules (Chvapil 1973 and 1976; Mahadevan et al 1990; Bray and Bettger 1990; Pasternak et al 1992; Kaszuba and Hunt 1990). Zinc can also suppress the leakage of metabolites out of cellular pores or lesions created by various bacteria and viruses. In addition, zinc also increases the activity of various enzymes that help cells withstand stress, such as glucose transporters (Pasternak 1990), ecto-nucleotidases (Meftah et al 1991), and certain protein kinases (Zalewski 1991). Zinc also increases the integrity of internal multicellular membranes, such as blood vessel walls (Hennig et al 1992), and it appears to have a bifunctional interaction with actin; at low-to-moderate concentrations of zinc, actin increases cell membrane permeability, while at high concentrations of zinc, actin reduces membrane permeability (St. Onge and Gicquaud, 1990).

In short-term tests, zinc has been shown to be harmless or beneficial inside the vagina (Chvapil et al 1978a and 1978b; also see Williams 1980 and Chvapil 1980). These reports describe research using guinea pigs, rabbits, and human volunteers to study whether zinc would be an effective contraceptive. It was only about 80% effective on a single-event basis, so interest in its use as a potential contraceptive died out. However, during those tests, it was shown that (1) most of the zinc introduced into the vagina became bound to vaginal fluids or cells, and was washed out of the vagina within a few days by the natural flow of fluid and the exfoliation of epithelial cells from internal vaginal surfaces; (2) zinc content in vaginal tissue in treated animals was not significantly different than in control animals; and, (3) zinc did not cause any significant swelling, redness, tenderness, or histological changes to vaginal membranes.

Indeed, when introduced into the vagina along with other contraceptive agents or collagen sponges, zinc played a beneficial role; it prevented the generation of offensive smells ("malodors") that were occasionally encountered when untreated sponges were removed, and it reduced or prevented the irritation or swelling caused by such other agents in the absence of zinc. These are consistent with zinc's utility as a a mild broad-spectrum antibacterial and antifungal agent, and with its additional utility as a topical healing agent.

These beneficial effects become especially interesting in light of a report which stated that nonoxynol, a surfactant that attacks lipid membranes, actually increased the risk of HIV infection among prostitutes (Kreiss et al 1992). There is no question that nonoxynol can destroy HIV particles, by attacking the lipid envelopes which surround them. However, if used with high frequency (as occurred among the prostitutes in Kenya who were studied), nonoxynol can also create vaginal lesions, which are essentially open sores. These open sores can become entry ports for HIV particles to pass through the protective barrier of the skin and reach the bloodstream. Accordingly, among people who use nonoxynol as a contraceptive or condom lubricant, nonoxynol can be alternated with a lubricant containing zinc, to promote healing of any nonoxynol-induced lesions.

Zinc can also promote and accelerate the healing of lesions caused by other sexually transmitted diseases, including herpes and syphilis. Such other diseases have been shown statistically to increase the risk of HIV infection (e.g., Holmberg et al 1988) and it has been estimated that lesions from sexually transmitted diseases such as herpes and syphilis can increase the risk of HIV particles establishing an infection, after exposure during and after intercourse, by up to a hundred-fold. Accordingly, the ability of zinc to promote and accelerate the healing of such genital lesions is an important and highly beneficial factor in the use of zinc in a genital lubricant formulation.

Anti-Viral Activity of Zinc

Based on cell culture tests, zinc has been reported to be effective against numerous different types of mammalian viruses, including sindbis virus (Bracha et al 1976), foot and mouth disease virus (Firpo and Palma 1979), vaccinia virus (Zaslavsky et al 1979), aphthovirus (Sharma et al 1985), and rhinoviruses (Korant et al 1976A and 1976B; Godfrey et al 1988). These items are discussed in more detail in above-cited application Ser. No. 737,169, the contents of which are hereby incorporated by reference. That patent application focuses on the herpes simplex virus type 2 (HSV-2), which causes genital herpes. The use of zinc salts (primarily zinc sulfate, which causes substantial burning and irritation in most patients) to treat established herpes infections is discussed in Gordon et al 1975, Fahim et al 1980a and 1980b, Tennican et al 1979 and 1980, Wahba et al 1980, Brody et al 1981, Eby and Halcomb 1985, and U.S. Pat. Nos. 4,465,666 and 4,762,715 (Lukas et al). U.S. Pat. No. 4,407,818 (Lionelle and Staffa, 1983) also discloses a zinc oxyacetate complex which was reported to be effective against herpes. None of those references relate to AIDS or the HIV virus.

In a patent application filed under the Patent Cooperation Treaty, number WO 8702246, William Sergio suggested that the risk of infection with AIDS might be reduced by topical administration of zinc salts and other compounds that generate anions having charges greater than one. Sergio's reference to anions was mistaken, since an anion is a negatively charged ion, while zinc ions are cations (positively charged). Sergio also states that his preferred salts are zinc phosphonoformate and/or zinc tungstate; however, it is likely that the use of either of those compounds in a sexual lubricant would cause irritation and toxicity. His suggestion concerning zinc tungstate appears to be based on the tungsten compound HPA-23, which, as Sergio conceded elsewhere, has "serious side effects" (Sergio 1988). The Sergio proposal apparently never issued in any allowed patents, and it was also contradicted by data gathered by researchers at the National Cancer Institute and elsewhere, indicating that in their assays, zinc had no beneficial effect against HIV.

One object of this invention is to provide an agent and a method for reducing the risk that a person who has previously not been infected by HIV will become infected if that person has sexual intercourse with someone who carries the virus.

Another object of this invention is to disclose a method for utilizing a non-toxic, non-irritating anti-HIV agent in a carrier formulation comprising a non-irritating sexual lubricant that can be spread on the genitals during sexual intercourse to reduce the risk that an uninfected person will become infected by HIV.

Another object of this invention is to provide a sexual lubricant which contains an effective topically-active anti-HIV agent which is non-toxic and non-irritating to the genitals and urethral and vaginal membranes.

The discussion and claims which follow focus primarily on zinc salts as anti-viral agents. However, co-pending U.S. application Ser. No. 07/816,278, cited above, also contained an additional item which is incorporated herein by reference. It disclosed the use of relatively small fragments of the human CD4 peptide, which can bind to the viral gp120 protein, in a topical lubricant. One of the key aspects of that disclosure was the disclosure that such CD4 fragments could be coupled to polymeric backbones, to increase their effectiveness. This would render the CD4 fragments analogous to fishing hooks tied to a fishing line; it would only require a single CD4-gp120 binding reaction to ensnare a viral particle and reduce its motility and its ability to contact and infect susceptible cells. By contrast, prior proposals to use soluble CD4 fragments suffer from a major limitation: each soluble CD4 fragment can bind to and inactivate only a single gp120 peptide, and every HIV particle has dozens of gp120 peptides on its surfaces. As noted above, the disclosure that CD4 fragments should be attached to polymeric backbones to increase their effectiveness in a topical lubricant is incorporated herein by reference.

SUMMARY OF THE INVENTION

This invention relates to a method of using, during intercourse, a genital lubricant containing a non-toxic, non-irritating zinc salt. The lubricant is spread upon genital surfaces to create an anti-viral chemical barrier that reduces the risk of infection by the human immunodeficiency virus (HIV), the virus that causes AIDS. Suitable salts include zinc acetate, zinc propionate, and other non-irritating water-soluble organic salts that dissociate readily.

Zinc reduces HIV infectivity by at least two mechanisms. First, it forms crosslinking bonds with cysteine or histidine residues in proteins. Inside a vaginal cavity, these crosslinking bonds can bind HIV viral particles to each other, to proteins in vaginal fluids, and to epidermal or epithelial cells that will soon be sloughed off from the genital surfaces. This agglomerates the viruses or binds them randomly to proteins or cells that cannot be infected.

In addition, zinc promotes healing and closure of lesions, abrasions, or other skin deficits (zinc is a soothing and healing agent in numerous topical formulations, such as diaper rash ointments and calamine lotion). Since lesions, abrasions, or other breaches in the skin can serve as entry ports that allow HIV to penetrate the skin and reach the bloodstream, this skin healing effect is highly beneficial and reduces the risk of HIV infection.

An assay procedure is also disclosed for evaluating candidate antiviral agents for use in topical genital lubricants. This assay involves a two-stage incubation protocol. In the first incubation step, HIV particles are mixed and briefly incubated with a candidate anti-HIV agent, at a concentration approximating the levels that will exist inside the vagina after intercourse using a lubricant containing the agent; such concentrations can greatly exceed the concentrations of an anti-viral agent that can be tolerated in the bloodstream. In the second incubation step, the agent-and-HIV mixture is diluted until the anti-HIV agent is not toxic to lymphocytes, then mixed with lymphocytes. The agent-virus-lymphocyte mixture is cultured, and the infectivity of the treated viruses is compared to identically diluted but untreated viruses.

BRIEF DESCRIPTION OF THE FIGURES

FIG. 1 shows that HIV infectivity was completely eliminated when concentrated viral stocks were incubated with 1% zinc acetate for 2 hours before the zinc-virus solution was diluted (1:30) and mixed with susceptible lymphocytes.

FIG. 2 shows that HIV infectivity was reduced and delayed when concentrated viral stocks were incubated with 1% zinc acetate for 2 hours before the zinc-virus solution was diluted (1:100) and mixed with lymphocytes.

DETAILED DESCRIPTION OF THE PREFERRED EMBODIMENTS

Figure 3:
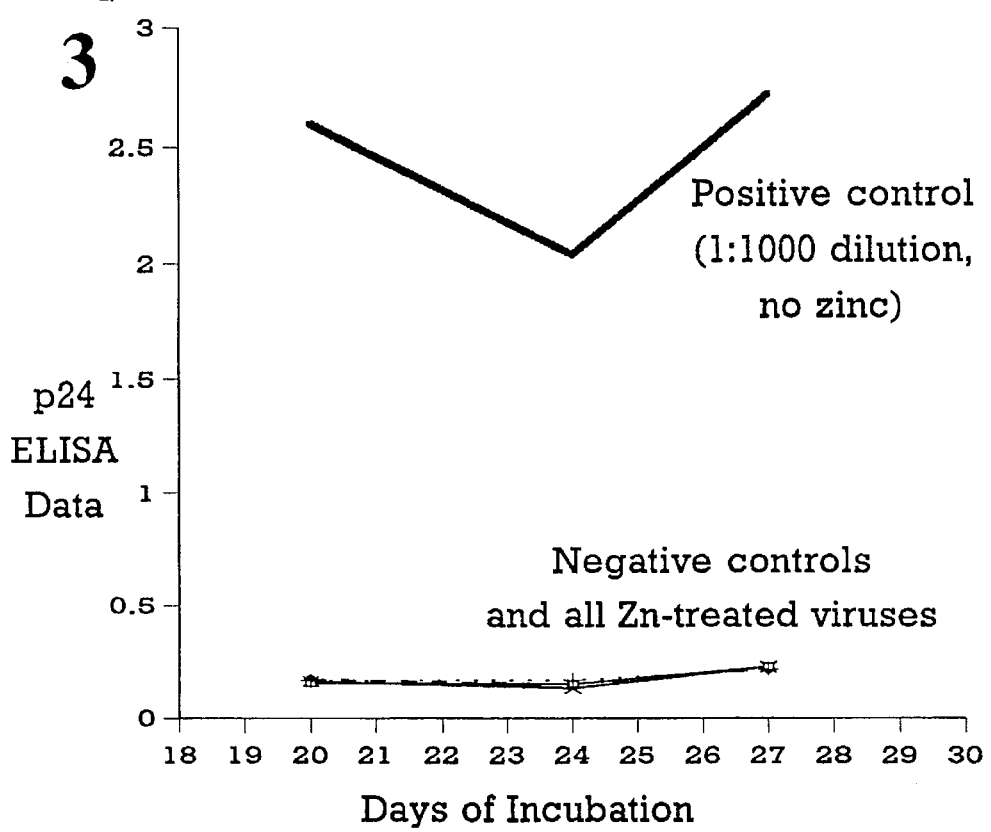
FIG. 3 shows that HIV infectivity was completely eliminated when various dilutions of high-titer viral stocks were incubated with 1.5% zinc acetate for 2 hours.

This invention relates to a method of reducing the risk of infection by human immunodeficiency viruses (HIV). This method comprises the use, during sexual intercourse, of a genital lubricant containing a non-irritating water-soluble zinc salt (such as zinc acetate, zinc propionate, or zinc lactate) at a concentration that does not irritate the genitals.

As used herein, "genital lubricant" refers to a fluidized substance that is spread across the surfaces of the genitals (such as the shaft of a penis or inside a vagina) shortly before or during sexual intercourse, and which remains in contact with the genital surfaces during intercourse, for the purpose of establishing a chemical layer between the genital surfaces of the sexual partners. It does not include ointments, lotions, or other substances that are spread on the genitals or inserted into the vagina for purposes other than to provide a fluid coating which covers essentially the entire surface of a penis or vagina during intercourse. For example, it does not include ointments intended to reduce itching or promote the healing of herpetic lesions during an outbreak of genital herpes; since people are advised to abstain from intercourse during outbreaks of herpes lesions, such ointments and lotions are not intended or suitable for use as lubricants during intercourse. Similarly, it does not include contraceptive foams, gels, or other fluids that are injected deep into the vaginal cavity or placed inside diaphragms for contraceptive purposes.

A zinc salt as described herein will be one ingredient in a lubricant formulation comprising either an aqueous fluid (such as a gel) or an emulsion containing an aqueous phase. The carrier fluid can be physiologically inert, and can serve merely as a vehicle for the zinc salt; alternately, the carrier fluid can have one or more other ingredients that serve therapeutic or other useful purposes, as discussed below. Preferably, the carrier fluid should contain a lubricating agent such as glycerin which will both (1) reduce friction during intercourse to create a pleasurable and comfortable experience, and (2) coat the epidermal or epithelial surfaces to create a viscous mechanical barrier that will further help to reduce contact between viruses and potentially susceptible cells.

References to genital surfaces or genital lubricants do not require that all genital surfaces must be contacted by the anti-viral agent of this invention. For example, if a lubricant is spread across the outer surface of a condom immediately before intercourse, then the lubricant will be spread across the epithelial surfaces inside the vagina and will be covered by the claims, even though the lubricant will not directly contact the penis, which remains inside the protective barrier of the condom.

The lubricant remains in place throughout intercourse. As described below, the zinc salt will reduce the risk that an uninfected person will become infected, if he or she has sexual intercourse with someone infected by HIV. The zinc salt should not be regarded as a treatment agent for someone already infected by HIV; instead, it is a preventive or prophylactic agent, to protect people who are not infected.

A zinc-containing genital lubricant should not be regarded as a guaranteed, 100% reliable preventive agent; instead, it merely reduces the risk of infection. Accordingly, the lubricants disclosed herein preferably should be used with a condom. However, since some people refuse to use condoms even when they engage in sex with potentially infected partners, the lubricants of this invention can also be used without a condom. Such use will provide a much lesser degree of protection compared to proper use with a condom; however, it will still offer a significant reduction of the risk compared to totally unprotected intercourse.

A simple and easily applied standard to determine and compare the effectiveness of selected zinc salts at various concentrations in reducing the infectivity of HIV is as follows: a selected salt, at a desired concentration, can be mixed with a suspension of HIV particles in aqueous solution (such as an appropriate cell culture medium) and incubated for two hours at 37° C. To determine whether the HIV particles have been inhibited by this treatment, the incubated zinc-HIV mixture is diluted to a point where the zinc is not toxic to lymphocytes, and mixed with lymphocytes that can be infected by the HIV; the mixture is then cultured for a sufficient period to quantitatively assay HIV infection of the lymphocytes.

If a high-titer viral stock is used, the initial stock should be diluted by a factor of at least 1:10, since high-titer stocks contain extremely high viral concentrations that will never be encountered in nature, particularly not among people in the early or middle stages of infection, who pose a significant risk of having unprotected intercourse with people who are not infected. Since zinc salts apparently inactivate HIV particles by crosslinking them randomly to each other and to cells that cannot be infected, rather than by other, more aggressive viricidal mechanisms that attack and destroy HIV peptides or particles, the anti-HIV activity of zinc salts has been repeatedly missed by other researchers who have screened such salts using conventional viricidal screening assays.

Anti-Viral Activity of Zinc: Molecular Mechanisms

A number of reports in the medical and scientific literature have identified various mechanisms that allow zinc salts to inhibit various viruses other than HIV. These reported mechanisms include interactions of zinc with post-translational processing of capsid polypeptides in rhinoviruses (Korant et al 1974 and Butterworth and Korant 1975), inhibition of DNA polymerase in herpes virus (Shlomai et al 1975 and Fridlender et al 1978), interference with protein synthesis in herpes viruses (Gupta and Rapp 1976), inhibition of thymidine kinase accumulation and a possible alteration of RNA synthesis in vaccinia virus (Zaslavsky 1979), and interference with procapsid synthesis in foot-and-mouth disease virus (Firpo and Palma 1979).

However, all of these reported mechanisms presumably occur inside infected cells, and they cannot readily explain the HIV inhibitory effects described in Examples 2 and 3 or the virus precipitation effects described in Example 4, below.

Therefore, without restricting this invention to any theory or specific mode of interaction at the atomic level, the Applicant wishes to suggest a possible explanation. Divalent zinc ions ($Zn^{++}$) apparently can inactivate viruses by a mechanism that involves binding to two or more viral particles, thereby forming crosslinked viral aggregates that are less soluble and more subject to steric hindrance and other inhibition in their ability to permeate into the bloodstream and contact lymphocytes. In addition, $Zn^{++}$ ions can cause crosslinking of viral particles to any other proteins which they happen to contact, such as proteins on the surfaces of relatively inert cells that have been or soon will be sloughed off from an epithelial or epidermal surface.

These binding and crosslinking processes can be most easily grasped by thinking of zinc ions as a form of "Viral Super-Glue."

The hypothesis of non-specific binding and crosslinking is based on an important class of interactions between zinc and certain types of amino acid residues in proteins. It is well known that $Zn^{++}$, which has a fairly large positive charge, binds to the localized negatively charged unshared electron pairs in cysteine and histidine residues in proteins. By binding to two or more cysteine or histidine residues in different protein molecules, a zinc ion can form a crosslinking bond between two or more different proteins.

This type of crosslinking bond formation is similar to the bonds formed in a important class of proteins called "zinc-finger" proteins (see, e.g., Nardelli et al 1991). In zinc finger proteins, which are involved in the transcription of DNA genes to produce messenger RNA, four different cysteine or histidine residues form crosslinking bonds with a single zinc ion, in a tetrahedral configuration. This bonding arrangement holds the protein in a special three-dimensional conformation that creates a "finger" structure. The zinc ion is located at the base of the finger, which is a loop structure that extends outwardly and then returns to the zinc ion. When the protein is active, this finger extends down into the deep groove of the DNA double helix. The protein travels along the gene, and when a specific DNA sequence is located and "recognized" by the amino acid residues in the protein finger, the transcription process is activated. This leads to the formation of messenger RNA. Zinc finger proteins also exist in HIV (Rice et al 1993).

The gp120 protein, which is exposed outside the viral envelope on the surface of HIV particles, has numerous cysteine and histidine residues. The sequence reported for the gp120 protein of the BH10 viral isolate (also called the HTLV-IIIb strain) contains 18 cysteine and 7 histidine residues, which were highly conserved in other viral isolates (Starcich et al 1986). Several other isolates reported in Starcich et al 1986 contained even higher numbers of histidine residues than in the BH10 isolate.

The ability of cysteine or histidine residues to form stable crosslinking bonds with zinc indicates that in the presence of a dissociated zinc salt in solution, a single cysteine or histidine residue (or perhaps two such residues) in a gp120 molecule can bond to a zinc ion without forming all four bonds that would complete the tetrahedral structure found in zinc finger proteins. This would leave the partially-bound zinc capable of forming additional bonds with other molecules, such as a gp120 protein on another viral particle (this would form viral dimers or aggregates), or proteins on the surfaces of epidermal or epithelial cells which either cannot be infected by HIV or which probably will be sloughed off from the surface before the viral replication cycle is complete.

This hypothesized process is consistent with the results described in Example 3, which indicated that mixing a zinc salt with a viral suspension reduced the number of viral particles that remained suspended in an aqueous solution.

It should be emphasized that the teaching of this invention does not depend on this or any other presumed or apparent atomic or molecular mechanism; instead, it depends on the practical discovery and teaching that a water-soluble zinc salt, at a concentration that can be tolerated with no irritation in a genital lubricant used during intercourse, can greatly reduce the infectivity of HIV.

Solubility and Dissociation of Zinc Salts

To be suitable for use as described herein, a zinc salt must have at least three major characteristics: (1) it must have a substantial degree of solubility in water; (2) it must dissociate at a sufficiently high level to release substantial quantities of zinc ions ($Zn^{++}$); and, (3) it must not irritate the genitals or cause other adverse effects when mixed with a suitable carrier fluid and used as a topical lubricant during intercourse.

Due to their high solubility in water and their high rates of ionic dissociation (as indicated by low pK values, discussed below), zinc acetate, zinc propionate, zinc lactate, and various other organic salts of zinc listed in Table 1 are preferred for use in this invention. Zinc gluconate is also preferred, even though it is less soluble and has lower ionic dissociation rates than various other salts, since it is widely consumed by humans as a mineral supplement and has a long-established record of being completely safe and well tolerated in the body. Zinc gluconate contains two anions from gluconic acid, a carboxylic acid derivative of glucose. Other comparable sugar-acids such as glucaric acid, glucuronic acid, galacturonic acid, and mannuronic acid are also good candidates for use as described herein.

Various other organic salts that appear to be less suitable include zinc salicylate, citrate, oleate, benzoate, laurate, and tartrate. These are relatively insoluble in water

TABLE 1

PROPERTIES OF VARIOUS ORGANIC SALTS OF ZINC

| Salt | Solubility (g/liter) | Molecular weight | Molar solubility (moles/liter) | Reported pK values |
|---|---|---|---|---|
| Zinc acetate | 300 (25° C.) | 183.4 | 1.64 | 1.03 |
| Zinc propionate | 320 (15° C.) | 211.5 | 1.51 | 1.01 |
| Zinc butyrate | 107 | 275.6 | 0.4 | 1.00 |
| Zinc formate | 52 (20° C.) | 155.4 | 0.33 | $pK_1 = 0.6$, $pK_2 = 0.95$ |
| Zinc gluconate | 127 (25° C.) | 455.7 | 0.28 | 1.70 |
| Zinc glycerate (dihydroxy-propionate) | NA | 275.6 | NA | 1.80 |
| Zinc glycolate (hydroxyacetate) | NA | 215.5 | NA | 1.92 |
| Zinc lactate | 57 | 279.5 | 0.20 | 1.86 |

Sources:
Cannan and Kibrick 1938
Sillen and Martell 1964 and 1971
CRC Handbook of Chemistry and Physics, p. 4-116 to 118 (71st Edition, 1990),
Solubility of Inorganic and Metal Organic Compounds, 4th Edition (1965)

or have high pK values (low ionic dissociation).

Certain other organic salts that were initially evaluated had various other drawbacks. For example, zinc valerate, although soluble in water, has an unappealing dirty-looking color and an unpleasant odor, and zinc stearate has an unpleasant odor. Even though neither caused irritation in forearm or male genital tests, they were not tested vaginally or during intercourse.

Zinc oxide was also tested and found to be non-irritating during intercourse. It was expected to be non-irritating, since it is the main active ingredient in calamine lotion and various ointments that are spread on the bottoms and genitals of babies to cure diaper rash. However, zinc oxide is not a salt in the normal chemical sense; it is formed when an atom of oxygen forms a double-bond with an atom of zinc. Dissociation of zinc oxide to release zinc ions occurs gradually when zinc oxide contacts body fluids (Agren 1990), but this is a very slow process compared to the dissociation of the salts discussed herein. However, vaginal fluids tend to be relatively acidic, which presumably would increase the rate of ionic dissociation, and there may be enzymes or metabolic pathways in vaginal fluids or semen that would increase the rate of dissociation of zinc oxide to release zinc ions. Therefore, the potential of zinc oxide to function as an anti-viral agent in a topical genital lubricant should not be ignored, especially in view of its other benefits when applied topically (particularly its ability to promote healing of skin abrasions and lesions). Accordingly, although the Applicant is not aware of any published reports indicating that zinc oxide has anti-viral activity, its anti-HIV activity can be determined through in vitro or in vivo tests as described below or otherwise known in the art. If zinc oxide is shown to have anti-HIV properties in such tests, it might be suitable for use as described herein.

It should also be noted that zinc oxide is bright white, while zinc acetate and most other soluble organic salts are clear and transparent when dissolved in water or aqueous gels. To minimize staining or discoloration of clothes, bedsheets, and other items, most people prefer clear, transparent gels for genital lubricants.

Each salt listed in Table 1 is formed by coupling two anions to one atom of zinc. Each anions is formed by dissociation of a hydrogen proton from a carboxylic acid group (RCOOH→RCOO$^-$, where R represents any molecular group that a carboxylic acid group is attached to). Since two anions bond to one zinc atom, the general formula of these salts is $Zn(RCOO)_2$. Alternately, a dicarboxylic acid (an organic molecule having two carboxylic acid groups at different locations on the molecule) such as malonic or maleic acid can be used if desired.

For simplicity, the anti-viral activity of a zinc salt can be presumed to arise from free divalent zinc ions ($Zn^{++}$). This is not a rigid rule; ionic association and dissociation are reversible reactions that establish equilibrium in a liquid, and a partially dissociated zinc ion (such as $CH_3COOZn^+$, formed when one of the two acetate anions in zinc acetate dissociates) can form an initial crosslinking bond with a cysteine or histidine residue on a protein molecule. The second acetate ion can then dissociate and leave, allowing the zinc ion to form a second crosslinking bond with a second protein molecule, thereby forming a crosslinking bond between the two protein molecules. Because the net result is the same, it is simpler and reasonably accurate to assume that (1) the formation of protein crosslinking bonds involves $Zn^{++}$ ions, and (2) the ability of a certain zinc salt in a genital lubricant to reduce the risk of HIV infection will be proportional to the quantity of $Zn^{++}$ ions released by that salt.

Three factors have primary importance in determining the concentration of free $Zn^{++}$ ions in an aqueous solution if a certain zinc salt is dissolved in that solution. Those factors are:

(1) The quantity of the salt dissolved in the carrier fluid, which can be limited by the solubility of a certain salt in water. Although a 5% w/v solution of zinc acetate in water does not approach the solubility limits of zinc acetate in water, a 5% solution of another salt such as zinc gluconate might approach or even surpass the solubility limits. Also, as a salt begins to approach a solubility limit, the likelihood increases that some portion of a dissolved salt might precipitate out of solution, creating potentially abrasive particles that would be very disadvantageous. Accordingly, zinc salts with high solubility in water are strongly preferred. Solubility is often expressed as grams of salt per 100 cubic centimeters (0.1 liter) of saturated solution. That figure can be converted into a grams/liter basis by multiplying it by 10.

(2) The quantity or fraction of the salt that dissociates in water, to release cations and anions. This is usually expressed on a base 10 logarithmic scale using so-called "pK" values, which are referred to by various authors as equilibrium constants, stability constants, or dissociation constants. In a manner comparable to pH calculations (which indicate acidity), pK values are calculated by dividing the molar concentration of dissociated ions by the molar concentration of non-dissociated molecules. If a pK value for a certain salt is low, the level of ionic dissociation for that salt is high. This is comparable to saying that if the pH of a solution is low, the acidity of the solution is high.

(3) The molecular weight of the salt, which allows a weight concentration to be converted into a molar concentration. The molecular weight of zinc acetate is 183.4, so 183.4 grams of zinc acetate is equal to one mole ($=6.02\times10^{23}$ molecules). Molar concentrations are expressed in molar units; for example, a 1M solution refers to a solution having 1 mole of a compound per liter of solution, while a 1 millimolar (1 mM) concentration refers to a thousandth of a mole per liter. Also, it should be kept in mind that the weight of a zinc salt is substantially higher than the weight of elemental zinc. For example, the molecular weight of zinc acetate is 183.4, while the molecular weight of elemental zinc is 65.4. This ratio of molecular weights is about 3 to 1; therefore, three grams of zinc acetate contain about one gram of elemental zinc.

Additional information on the solubility and dissociation of various zinc salts is contained in Table 1 and in Sillen and Martell 1964 and 1971, Cannan and Kibrick 1938, Linke 1965, and the *CRC Handbook of Chemistry and Physics*. Regrettably, since there are various ways to measure ionic dissociation of salts, pK values are not always consistent between different publications. In addition, some publications do not clearly indicate whether a certain pK value reflects partial or complete dissociation of a divalent salt. Nevertheless, the published values compiled in Table 1 clearly indicate that certain salts (such as zinc acetate and propionate) have high dissociation rates, while other salts such as zinc gluconate have lower but substantial dissociation rates.

The inorganic zinc salts tested to date, such as zinc chloride and zinc sulfate, have irritated forearm skin or genitals at the concentrations tested. Therefore, they are not preferred; however, some inorganic salts (particularly zinc sulfate, which has been widely used to treat outbreaks of genital herpes lesions) might be suitable in some contexts, such as in low concentration formulations that contain ingredients which can soothe or mask low levels of irritation.

This invention also anticipates the use of a lubricant gel containing two or more zinc salts or other zinc compounds. For example, a genital lubricant as described herein can contain zinc acetate or propionate to provide a high level of initially available zinc ions, along with a second salt such as zinc gluconate or another compound such as zinc oxide, to create a longer-lasting plateau of elevated zinc concentrations.

Development of the Two-Stage Incubation Assay

After becoming interested in the potential of zinc as a topical anti-viral agent, the Applicant submitted samples of several zinc salts (including zinc acetate and zinc gluconate) to the Drug Synthesis and Chemistry Branch of the National Cancer Institute (NCI) for evaluation in a screening test against HIV. The NCI plays a major role in research on HIV and AIDS, since retroviruses (which carry RNA rather than DNA; HIV viruses are retroviruses) were initially discovered and studied as cancer-causing agents. The NCI's Drug Synthesis and Chemistry Branch cooperates with the Anti-Viral Evaluation Branch of the NCI, and together, they run a public-service screening program. They will evaluate any compound submitted to them, using a standardized assay described in Weislow et al 1989. This assay involves contacting lymphocytes with HIV and with a candidate antiviral agent at the same time, culturing the cells for a sufficient period of time to allow the viruses to infect the cells and replicate, and analyzing the cell culture to determine whether the agent inhibited infection or replication.

When the Applicant submitted several zinc salts for evaluation, the scientists in charge of the NCI's screening program returned the zinc salts without even opening them. The NCI's letter of response, dated Aug. 8, 1991, stated as follows: "After careful consideration, we have decided not to test your zinc salts in our AIDS-antiviral assay . . . We have tested 36 zinc-containing compounds in our in vitro AIDS screen, including zinc gluconate (test results of this inactive compound, NSC 619899, are enclosed . . . ). None of these materials has demonstrated any activity worth pursuing . . . Based on these results, we don't believe that your compounds will show activity in our assay."

To the best of the Applicant's knowledge, the tests carried out by the NCI indicated that the zinc salts they tested became toxic to lymphocytes at concentrations below the levels that were anti-virally effective. Since lymphocyte toxicity occurred before anti-viral efficacy was manifested, the zinc salts were regarded as therapeutically useless by the NCI.

However, the Applicant realized that the NCI's assay does not and cannot indicate whether an anti-viral agent might be effective in a topical genital lubricant which is spread across the surface of the skin rather than being injected into the blood or ingested orally. By the time he received the NCI's letter, the Applicant had already discovered that when zinc acetate or gluconate were dissolved in K-Y Lubricating Jelly (trademark of Johnson & Johnson, New Brunswick, N.J.) at a concentration of up to 5% weight per volume (w/v), the mixture caused no irritation or adverse effects when used as a genital lubricant during a complete act of heterosexual intercourse. This result is described in Example 1.

When the Applicant examined the NCI data printout for zinc gluconate, he realized that the concentration of zinc that can be tolerated in a surface lubricant is roughly a hundred to a thousand times higher than the concentration that can be tolerated by lymphocytes in the bloodstream. Zinc exerts inhibitory or cytotoxic effects on lymphocytes at about 50 micrograms (ug) per milliliter of fluid (and possibly even lower), and it becomes highly toxic to lymphocytes by the time the concentration reaches 500 ug/ml. By contrast, the 5% w/v concentration tested by the Applicant in a topical lubricant with no adverse effects contained 50,000 ug/ml, which was 100 to 1000 times higher than the levels that were toxic to lymphocytes.

Most of the zinc in a genital lubricant will remain outside the skin. Some quantity might permeate into the shallow surface layers of epidermal or epithelial cells, but those cells are relatively inert metabolically and will be sloughed off within a few days. If used topically, in a genital lubricant, the great majority of the zinc will never reach the bloodstream, and any small quantities that do reach the blood will be handled by the normal metabolic processes that regulate blood concentrations (summarized above and discussed in Vallee and Falchuk 1993).

When it became clear to the Applicant that the assays used in the NCI screening protocol could not identify or evaluate potentially useful topical agents, the Applicant developed a different protocol. When the Applicant contacted the proper officials at the Anti-Viral Evaluation Branch of the NCI and discussed the proposed assay with them, the officials stated that they could not perform such assays, but that this approach was worth pursuing and the assays could be done at a privately operated laboratory which works with HIV, such as Cambridge Biotech, Inc. (Rockville, Md.; this company was subsequently renamed as Biotech Research Labs, Inc.). Accordingly, the Applicant contacted that laboratory and requested them to do the assays described in Example 2.

Briefly, the first round of assays involved creating a mixture of zinc acetate in aqueous solution, and mixing the zinc solution with a cell-free suspension of HIV particles at a final concentration of 1% zinc acetate on a weight per volume (w/v) basis. The zinc salt was incubated with the viruses for two hours at 37° C. This brief incubation period was intended to simulate the interactions that will occur between zinc and viruses inside the vagina, if a woman uses a lubricant containing zinc during intercourse with a male infected by HIV and they do not use a condom. During this brief incubation period, the zinc will not cause any vaginal or genital irritation even though the same concentration would be highly toxic to lymphocytes if it entered the blood.

At the end of the 2 hour initial incubation, the zinc/virus mixture was diluted by a series of dilutions ranging up to 1:100. The diluted mixtures were then mixed with HIV-susceptible lymphocytes (the H9 cell strain was used) and incubated at 37° C. for 20 days, using triplicate samples for each dilution. Aliquots were removed from each cell culture after 6, 10, 13, 16, and 20 days, and tested to evaluate the quantity of viruses being generated in each cell sample. The tests involved an ELISA assay (an enzyme-linked immunosorbent assay), using monoclonal antibodies that bind to the viral p24 protein.

The results are displayed in Table 2 and FIG. 1. These results indicate that the zinc pre-treatment greatly reduced the infectivity of the HIV virus.

This positive result had never showed up in previous assays, such as the assays conducted by the NCI, since the NCI assay protocol did not use any method of modeling a high-concentration contact and incubation period outside the epidermis, before contacting the lymphocytes with a lower concentration of zinc as would occur in the blood.

Two-stage incubation assays appear to offer a better method of assessing the potential anti-HIV activity of a topical genital lubricant than single-step assays. During or after the second step of the two-step incubation procedure, conventional methodology can be used to assess viral infectivity or cell viability, such as ELISA or other assays involving antibodies that bind to viral antigens, or the chemical reaction described in Weislow et al 1989, which uses cellular conversion of tetrazolium to formazan as an indicator of cell viability.

Another published report (Resnick et al 1990) also deserves attention, since it arguably involves a two-step incubation protocol. In the Resnick et al protocol, the first incubation step (in which a candidate anti-viral agent is mixed with HIV with no lymphocytes present) lasts for only a minute before lymphocytes are added. Resnick's approach apparently was intended to provide a rigorous test that would demonstrate the high efficacy of nonoxynol, a surfactant that aggressively destroys the lipid envelopes that enclose HIV particles; compared to surfactants that attack and destroy the virus, virtually any other agent will be much less effective if tested in a one-minute incubation. However, nonoxynol was subsequently shown to have potentially adverse effects as a topical anti-viral agent; the same surfactant activity which destroys the lipid envelopes of HIV particles can also destroy the lipid envelopes of human cells and can create lesions in skin or mucous membranes, particularly if nonoxynol is used with high frequency. An incubation period of only one minute is probably inadequate to provide a reasonable screen for anti-viral agents that work by different mechanisms.

The results discussed in Pearce-Pratt and Phillips 1993 indicated that HIV-infected lymphocytes began the process of adhering to epithelial cells within about 20 to 30 minutes (as noted above, these tests were done in the absence of zinc, even though zinc alters cell membrane behavior, and even though zinc will always be present in semen). Accordingly, it appears that a two-stage incubation assay to evaluate potential agents for genital lubricants should provide at least about 20 minutes incubation before lymphocytes are added.

In addition, the cell—cell binding reactions studied by Phillips et al and others (e.g., Ho et al 1985 and Levy 1988) suggest another beneficial effect of zinc-containing topical lubricants. Although the high zinc concentrations in seminal fluid (100 to 500 ug/ml) are relatively toxic to lymphocytes, some viable lymphocytes survive in ejaculates, where their exposure to high zinc levels is relatively brief. Since viable HIV-infected lymphocytes in semen appear to increase the risk of transmission due to the lymphocyte-epithelial binding reactions discussed by Phillips et al, this may help explain the higher rates of HIV transmission among homosexual men than among other population groups, since many homosexual men suffer from reduced zinc levels in their semen (Weiner 1984 and Fabris et al 1988). However, in this invention, the toxicity to lymphocytes of high levels of zinc in a topical lubricant may be beneficial. If viable HIV-infected lymphocytes increase the risk of transmission, then a genital lubricant that contains zinc at levels which kill or inhibit lymphocytes would reduce the ability of HIV-infected lymphocytes to infect epithelial cells.

Carrier Formulations

In general, a carrier fluid used as a vehicle to carry the active anti-HIV agent in a genital lubricant must be physiologically tolerated when rubbed into the genital surfaces, as occurs during intercourse. Water-soluble carrier substances are generally preferred for use as described herein, for two reasons: (1) they can avoid the creation of hydrophobic-hydrophilic interfaces between the carrier substance and body fluids, which might tend to sequester the active anti-HIV agent and reduce its contact with viral particles that are suspended in aqueous body fluids; and, (2) most people who use sexual lubricants prefer to use water-soluble lubricants that can be washed off easily after intercourse without leaving a residue.

One class of preferred water-soluble carrier substances comprises aqueous gels. "Gel" is used herein to refer to an aqueous mixture that contains a thickening agent (as discussed below) and which has a viscous or semi-solid form at room temperature. Preferably, a sexual lubricant gel should become less viscous as it warms up from room temperature to physiological temperature (37° C. or 98.6° F.). The high viscosity at room temperature allows the gel to be applied conveniently before intercourse, without dripping off the fingers or genitals onto bedsheets or other surfaces. After intercourse begins and the gel warms up, it becomes less viscous and more slippery, providing comfortable lubrication during intercourse.

Gels can be mixtures of molecular components that are completely dissolved and non-particulate, such as water containing a soluble hydrophilic polymer as the thickening agent. Alternately, gels can be suspensions or colloidal solutions that contain insoluble or semi-soluble particles suspended in a liquid carrier medium; the suspended particles are usually microscopic in size, with average diameters measured in microns (for suspensions) or angstroms (for colloids). There is no clear-cut boundary between colloidal and soluble gels. For example, when powdered cellulose is mixed with water, the cellulose particles (which are hydrophilic) swell up and soften, so that they are no longer hard "particles" as that term is normally used, and some cellulose derivatives are transparent in water. These effects blur the distinctions between gel suspensions and soluble gels.

One water-soluble gel which has a variety of desired characteristics and which is widely used as a sexual lubricant is sold under the name "K-Y Lubricating Jelly" (Johnson and Johnson, New Brunswick, N.J.). It contains purified water, hydroxyethylcellulose as the suspending or thickening agent, glycerin as a lubricating agent, glucono-delta-lactate to prevent crystallization, chlorhexidine gluconate as a preservative, and sodium hydroxide to reduce the acidity. Those ingredients will be discussed in more detail below. A modified form of KY Lubricating Jelly sold by Johnson and Johnson contains propylene glycol residuals, which are a by-product of propylene oxide, a sterilizing agent.

It should be noted that "water-soluble carrier substance" is not necessarily limited to aqueous compounds (i.e., compounds which contain water). For example, many organic compounds containing hydroxyl groups are water-soluble even though they are not aqueous. Although solvent-type, low viscosity, or volatile compounds such as methanol or ethanol would not be physiologically suitable as sexual lubricants, other water-soluble hydroxylated compounds such as glycerin, polyethylene glycol, and polypropylene glycol have characteristics which can render them suitable; indeed, they are widely used as lubricating agents in cosmetics and aqueous gels applied to the skin.

Alternately, some types of emulsions can be used as sexual lubricants if desired. Emulsions are two-phase liquid systems containing very tiny droplets of one fluid suspended in a matrix of a second fluid (see, e.g., Becher 1965); one of the fluid phases is usually aqueous or hydrophilic, while the other is hydrophobic. Emulsions usually require a time-consuming emulsification step during manufacture to ensure that the inhomogeneous fluids are finely and evenly dispersed throughout the mixture, and they also usually require the use of a chemical surfactant (usually a molecule similar to a detergent, with a hydrophobic portion at one end and a hydrophilic portion at the other end) to keep the suspended droplets from coalescing and separating. In addition, emulsions and hydrophobic compounds (such as petroleum jelly) tend to leave residues that can be difficult to wash off, and some can weaken condoms, causing them to break. For these reasons, emulsions and hydrophobic compounds are not preferred by most people as lubricants during intercourse. However, some male homosexuals who engage in frequent anal intercourse reportedly prefer hydrophobic compounds; since such compounds do not rub off or rinse away easily, they offer prolonged lubrication compared to water-soluble lubricants. Accordingly, an emulsion containing a hydrophobic component can be used as a vehicle for an anti-HIV agent if desired. As used herein, terms such as "water-soluble carrier fluid" include aqueous gels, and emulsions having both an aqueous phase and a hydrophobic phase.

Suspending or Thickening Agents

In suspensions and emulsions, agents that increase the viscosity of the carrier liquid are often used to prevent insoluble particles or immiscible droplets from coalescing, settling to the bottom, or floating to the surface. In soluble gels, such agents are used to thicken the mixture and help ensure that all of the molecular components remain in a stable suspended condition and do not separate into layers based on density differences. Such agents are called suspending agents or thickening agents; as used herein, the terms "suspending agent" and "thickening agent" are used interchangeably.

Numerous types of physiologically-acceptable thickening agents are used in pharmaceutical and cosmetic preparations; see, e.g., pages 1304–1308 in *Remington's Pharmaceutical Sciences* (Gennaro 1990). These include compounds derived from plants, seaweed, or bacteria, such as powdered cellulose, chemically-treated cellulose derivatives such as hydroxyethylcellulose, acacia (also called gum arabic), agar, alginic acid and its salts (such as sodium alginate), carrageenan, gum tragacanth, and xanthan gum. Other substances derived from animals, such as lanolin (an exudate secreted by sheep into wool fibers) and gelatin (a mixture containing collagen, a protein) are also used as thickening agents in cosmetics and other skin care products. Various synthetic chemicals are also used, including carbomer (a common name for carboxypolymethylene), glyceryl monostearate, and povidone (polyvinylpyrrolidone). A mixture containing polyacrylamide in water, which functioned as both a thickening agent and a lubricating agent in a "physiological mucus" which assertedly was a suitable sexual lubricant, is described in U.S. Pat. No. 3,965,908 (Posthuma and Woodhouse 1976). Minerals such as colloidal silicon dioxide or clay are also used in some formulations.

Most sexual lubricant gels that are sold publicly contain cellulose derivatives as suspending or thickening agents. Derivatives such as hydroxyethylcellulose which generate a clear, uncolored, relatively transparent gel, rather than a milky-white or opaque gel, are preferred since they minimize staining of bedsheets, pajamas, and clothing.

Any physiologically acceptable thickening agent can be used as described herein, provided that: (1) it must provide suitable levels of viscosity; (2) it must be non-irritating to the genitals and mucous membranes when used as a sexual lubricant; and (3) it must not severely reduce the anti-viral activity of the anti-HIV agent contained therein. In addition, the viscosity preferably should decrease somewhat as the gel warms up from room temperature to physiological temperature.

Lubricating Agents

As used herein, "lubricating agent" refers to a chemical substance, other than water, which is incorporated into a sexual lubricant mixture for the purpose of reducing friction during intercourse.

Although any liquid (including water) can sometimes function as a "lubricating agent" in the broadest sense of the word, four characteristics distinguish a "lubricating agent," as that term is used herein, from water and other liquids which do not have the characteristics necessary for effective lubrication during sexual intercourse. First, a lubricating agent feels slippery and substantially more viscous than water when rubbed between the fingers. Second, lubricating agents should have an affinity for human skin; when applied to skin, they should spread smoothly and evenly across the contacted area. Third, a lubricating agent should remain in contact with the skin, clinging to it in a more substantial manner than water, which is easily wiped away. And fourth, a lubricating agent should have a low level of volatility; it should not evaporate quickly. The foregoing characteristics can easily be recognized on a practical level by rubbing a lubricating agent such as glycerin or mineral oil between the fingers. The nature and the durability of the lubrication provided by such a compound, and the differences between such agents and other liquids such as water, are readily apparent.

A genital lubricant which is physiologically tolerated during intercourse should not cause any significant adverse effects, such as irritation, tenderness, swelling, redness, or skin discoloration. It also must not pose a risk as a carcinogen, teratogen, or other toxic or hazardous agent. In addition, in contrast to non-physiological lubricants such as motor oil, physiologically acceptable lubricating agents should be either gradually broken down into innocuous substances in the body if they can be absorbed through the epidermis, or they should be of a nature that allows them to be secreted by the vagina and washed cleanly from the skin, so that they will not foul and clog epidermal pores.

Several lubricating agents that are used in commercially available sexual lubricants satisfy all of these criteria, including glycerin (also called glycerine, glycerol, 1,2,3-propanetriol, and trihydroxypropane) and certain types of polyethylene glycol (PEG), such as PEG 200 or PEG 400 (the numbers indicate molecular weight averages). Various other polymers (such as polypropylene glycol, polyisobutene, and polyoxyethylene) and behenic acid and behenyl alcohol are also used as lubricants in cosmetics and other formulations that contact the skin. In addition, some sugar-alcohols such as sorbitol and some silicon compounds such as polydimethylsiloxane are also used as skin-contacting lubricating agents.

Because glycerin, propylene glycol, polyethylene glycol, and polypropylene glycol have long been used in sexual lubricants and other skin-contacting formulations with no adverse effects, they are preferred for use as lubricating agents in the anti-HIV lubricants of this invention. The suitability of any other candidate lubricating agent in a sexual lubricant as described herein can be determined through routine experimentation in humans to ensure that it will not cause irritation or other adverse effects.

The presence of a lubricating agent such as glycerin or polyethylene glycol is not essential to this invention; for example, a gel containing nothing but water, a thickening agent, and one or more of the anti-HIV agents described herein can be used as a "sexual lubricant" as that term is defined and used above. However, the addition of friction-reducing agents such as glycerin to sexual lubricants can enhance their comfort and appeal and thereby increase their consistent use and their anti-viral effectiveness.

Additional Agents

Various other components, including preservatives (such as chlorhexidine gluconate), anti-crystallization agents (such as glucono-delta-lactate), fragrances, coloring agents, alkaline or acidic agents to maintain the proper pH, and soothing or anti-swelling agents such as lanolin, aloe vera extract, or hydrocortisone can be added to the sexual lubricants described herein, provided that (1) any such additive should not seriously impede the anti-viral activity of the anti-HIV agent due to reactions such as the formation of molecular complexes which entangle, inactivate, or otherwise reduce the effectiveness of the anti-HIV agent; and (2) the additive should not irritate or have other adverse effects on the genitals.

Many cosmetics, shampoos, and other topically applied mixtures contain alcohols, detergents, or other chemicals that would irritate the skin if applied in concentrated form, but which are acceptable in low concentration, especially if any irritating effects are suppressed or masked by soothing or anti-swelling agents. Accordingly, a lubricant gel can contain a small quantity of a compound (including an anti-viral agent) that might be an irritant if present in concentrated form, provided that the formulation as a whole does not cause irritation.

Ointments and Lotions

Various ointment, lotion, and cream formulations are known to those skilled in the art; many of those can function as carriers for active ingredients. Several are described in detail in the *U.S. Pharmacopeia* and in various standard texts on cosmetics. In general, ointments, lotions, and creams are not as preferred as aqueous gels for use as sexual lubricants, for several reasons, including: (1) they often contain undesired ingredients which can be irritating and/or unnecessarily expensive, such as alcohols or emulsifiers; (2) many do not have the desirable temperature-dependent viscosity that sexual lubricant gels have; and, (3) many are hydrophobic and cannot be washed off easily.

Despite those drawbacks, various ointment, lotion, or cream formulations can be used as carrier fluids for a zinc-containing anti-HIV genital lubricant if desired, provided that the carrier fluid does not render the zinc salt ineffective as an anti-HIV agent, and provided that no components are present in concentrations that cause unacceptable levels of irritation to the genitals.

Skin and Vaginal Irritation Tests

To be suitable for use as described herein, a specific formulation containing a zinc salt at an anti-virally effective concentration must not irritate the genitals (as used herein, the term "genitals" includes the mucosal membranes inside the vagina and urethra). The level of genital irritation caused by any candidate formulation when used as a lubricant can be determined by using tests involving human volunteers, who should be fully informed of the entire procedure. It should be made clear to the volunteers that irritation tests do not involve viruses and do not pose any risk of infection; their sole purpose is to determine whether a certain formulation irritates the genitals, and if so, what percentage of the population is affected by such irritation (as discussed below). Whenever such tests are done, the subject population should not include women who might become pregnant during the course of the test.

A preferred sequence of tests is as follows. Each major step (forearm, male genital, and female genital tests) should use a passive test first, in which a formulation is applied and allowed to remain in place without being rubbed in. If no irritation arises, the formulation should be applied a second time and rubbed into the surface in a manner that simulates the effects of intercourse. In the first set of test, a zinc-containing formulation is tested on the relatively hairless portion of the forearm. If it does not irritate the forearm after being left in place passively for an hour or more, the next test involves a rubbing test on the forearm, and the next set of tests following that involves spreading it on the male genitals, which can be washed off more quickly and easily than female genitals if irritation arises.

If the formulation causes no irritation to male volunteers, it can be applied gently to a female volunteer, to the interior region near the opening of the vaginal canal which can be reached with shallow penetration. The woman should have tissues and a douche available before the test begins, to wipe and rinse out the substance if it begins to cause irritation.

During a passive test, zinc acetate caused a brief, relatively mild level of irritation in the vaginal canal of a female volunteer when dissolved in distilled water; however, it caused no irritation when mixed with K-Y Lubricating Jelly. Similarly, zinc propionate caused substantial irritation to the male urethra when mixed with water alone, but it caused no irritation when mixed with K-Y Lubricating Jelly. Accordingly, part of this invention rests on the discovery that some zinc salts, although irritating to the genitals when mixed with water only, are non-irritating when mixed with a complete lubricant formulation comparable to the formulation of K-Y Lubricating Jelly. Accordingly, it is recommended that any irritation tests should use a complete lubricating gel formulation as the carrier agent. This can be done easily, by mixing the zinc salt with a commercially available lubricant such as K-Y Lubricating Jelly.

If a formulation causes no irritation in a shallow passive test on females, it can be applied to the deeper areas inside the vagina, using a finger to apply it and rub it in gently. If no irritation occurs, the formulation can be tested during actual intercourse.

During the first test involving intercourse, the mixture preferably should be applied and tested only after a first act of coitus has been completed during which both partners climaxed, so that if any irritation does occur, neither person will be left in a state of sexual frustration, which severely aggravates any feelings of irritation.

It must be kept in mind that people vary in their skin sensitivity. By way of illustration, some people sunburn quickly, while others can withstand prolonged sunlight. In a similar manner, some people are highly susceptible to anxieties and mental suggestions of possible irritation, especially when the suggestion involves a sexual matter. Some people complain (and occasionally even display measurable symptoms) even when nothing more than an inert, innocuous placebo is being tested. Reichman 1985 provides a good example; during tests of acyclovir ointment applied topically to genital herpes lesions, identical fractions (29.6%) of the men in both the treated (acyclovir) and the untreated (placebo) groups complained of burning sensations regardless of whether they were treated with acyclovir or the placebo. Among women, the level of complaints of a burning sensation were nearly identical (53.3% for the acyclovir group, and 52.6% for the placebo group). The placebo consisted of polyethylene glycol, which is completely non-irritating for most people even when applied directly to active herpes lesions, as evidenced by the fact that over 70% of the men and nearly 50% of the women tested made no complaints of any burning sensation.

Accordingly, anyone studying irritation levels of a sexual lubricant formulations should take steps to reduce or minimize spurious or psychosomatic complaints. Volunteers who are prone to making such complaints should be screened out from the testing process, by asking all volunteers to first test a placebo gel. Volunteers preferably should be people who are familiar with and reasonably comfortable with sexual physiology; medical students, residents, nurses, and orderlies might offer a better test population than randomly selected patients from a clinic or hospital.

In addition, any researcher or counselor working with genital irritation tests of candidate formulations should themselves participate in such tests first, with their spouses or other partners, to develop a better understanding of the steps that should be followed and the cautions and reassurances that should be given to volunteers. For example, volunteers should be advised to have a box of tissues, a douche, and a shower available before the test begins, and they should be given a tube of ointment with a soothing agent such as hydrocortisone or lanolin. These steps can help alleviate anxieties and fears and reduce psychosomatic complaints by assuring volunteers that if a lubricant begins to cause any irritation, it can be taken care of quickly and easily. In addition, volunteers should be assured that the initial tests will involve dilute mixtures (1% or less); higher concentrations will be tested only in later tests, and only if a dilute formula causes no irritation.

In view of the widely varying skin sensitivity of different people, and in view of the high susceptibility of some people to any suggestion of potential irritation, references herein to "non-irritating" formulations refer to formulations that can be tolerated with no significant irritation, or with acceptably low levels of irritation, by a substantial number of the people tested. Such formulations can be used by a substantial fraction of the population, even though they might cause irritation in other people who have higher levels of sensitivity or who are more susceptible to psychosomatic suggestions of irritation.

In addition, anti-HIV lubricants described herein can be used even though they may well cause some level of irritation. Many people would regard a low level of mild irritation as a reasonable price for an added level of safety, comparable to the loss of sensitivity that accompanies condom use.

Concentrations and Packaging

Since people vary widely in their susceptibility to skin and genital irritation, the effectiveness of this invention can be enhanced by selling genital lubricants having a range of zinc concentrations. This approach is comparable to selling suntan lotions with various "sun protection factors" (SPF's), or contraceptive gels containing 1% to 10% nonoxynol. Purchasers are free to choose their preferred concentrations based on factors such as skin type and anticipated exposure level.

In a comparable manner, genital lubricants having a range of zinc concentrations can be sold, and people having varying sensitivities, sexual habits, and levels of concern or fear over the risk of HIV infection can choose the concentration they prefer. Highly sexually active, non-monogamous people who live in big cities with high rates of HIV infection might prefer a lubricant with a high concentration of zinc, even though it might cause some level of irritation, while people at lower risk might prefer to use lower concentrations.

Accordingly, this invention anticipates lubricants containing elemental zinc in the range of about 0.1% to about 15%, by weight or weight-per-volume (grams per milliliter). By way of comparison, some topical ointments that are not applied to the genitals contain more than 30% elemental zinc.

The genital lubricants described herein can be packaged in any suitable watertight package. One preferred package comprises a tube made of deformable metallic foil or plastic, crimped at one end and closed by a removable cap at the other end. Such tubes are commonly used to hold toothpaste, ointments, and gels such as K-Y Lubricating Jelly and contraceptive gels. When squeezed to dispense a small quantity of lubricant for use, a deformable tube will not seek to regain its original shape after the squeezing pressure is released. Unlike a rigid-walled jar, a deformable tube does not draw air into the tube; this minimizes oxidative discoloration or degradation of the lubricant remaining in the tube.

An alternate preferred package comprises a small, relatively flat, watertight plastic packet that contains a sufficient quantity of lubricant for a single use during intercourse (such as about 5 to 10 milliliters, or about 1 to 2 teaspoons). This type of small sealed packet, similar to a condom in a sealed packet, allows the lubricant to be conveniently and discretely carried without the bulk or conspicuousness of a tube.

This invention also teaches an article of manufacture comprising a sexual lubricant and packaging material as described above, wherein the lubricant contains a topically active anti-HIV agent as discussed herein, and wherein the lubricant is contained within the packaging material, and wherein the packaging material includes a label which indicates that the lubricant, if spread upon genitals during intercourse, is effective in reducing the risk of HIV infection. The label information helps to distinguishes the lubricants of this invention from prior art formulations which contained zinc sulfate for treating herpes lesions. Printed information on an article of manufacture must be regarded as one component of the invention as a whole, and it does not remove an article from the realm of patentability, so long as the invention as a whole satisfies the requirements of the patent statute.

EXAMPLES

Example 1: Irritation Tests Using Zinc Salts

The test subjects were a monogamous married couple free of genital herpes, HIV, or any other sexually transmitted viruses.

Zinc acetate (highest purity available) was purchased from Pfaltz and Bauer (Waterbury, Conn.). About 0.5 grams were mixed with several drops of distilled water at room temperature. Upon stirring, the zinc acetate dissolved completely. The aqueous mixture was rubbed into an area about 3 cm in diameter on the forearm of the male and caused no irritation.

Subsequently, about 0.5 grams of the salt were dissolved in a few drops of distilled water, then 10 ml K-Y Lubricating Jelly was added to form a gel mixture containing about 5% zinc acetate (w/v). This mixture was tested on the male genitals, passively at first and then with active rubbing. It caused no irritation in either test.

When 0.5 grams of zinc acetate was dissolved in distilled water and applied to the shallow region of the vagina by the female volunteer, it caused an unpleasant tingling or mild burning sensation, which subsided within about ten seconds and was not noticeable thereafter. However, when mixed with K-Y Lubricating Jelly (5% w/v as above) and applied to the shallow region of the vagina in a gel mixture, it caused no tingling, burning, or other unpleasant sensation in a passive test. Subsequently, it was applied and used as a sexual lubricant during a complete act of intercourse. Both people wiped off the excess with a tissue after intercourse, but neither person showered or washed off the lubricant until the following day. It caused no irritation to either person.

Zinc propionate (Pfaltz and Bauer) was tested in the same manner and caused no irritation.

Zinc gluconate (Ruger Chemical Company, Irvington, N.J.) was also tested the same way and caused no irritation. However, zinc gluconate is not highly soluble in water, so it was ground into a fine powder using a mortar and pestle and suspended in K-Y Lubricating Jelly by manual stirring. Although the gel mixture displayed a very slight roughness when rubbed hard between the forefinger and thumb, no abrasion was noticeable by either person during intercourse.

Zinc sulfate in crystalline form was purchased from Sigma Chemical Company (St. Louis, Mo.). One gram was ground into a fine powder using a mortar and pestle, then 15 ml of K-Y Jelly was added and thoroughly mixed. The mixture did not cause any irritation to the male's forearm, genital skin, or urethra, even when rubbed in actively. However, it caused a tingling or burning sensation when applied in a passive test to the female, so it was not tested during intercourse.

Zinc chloride in crystalline form was purchased from Sigma Chemical Company (St. Louis, Mo.). One gram was ground into a fine powder using a mortar and pestle, then dissolved in water and applied to the forearm of the male. It caused a burning sensation almost immediately and was not tested further.

Zinc oxide ointment (Walgreens Pharmaceutical Laboratories, Chicago, Ill.) containing 20% zinc oxide in an ointment base of white wax, petrolatum, and mineral oil was tested in a genital irritation experiment. Approximately 5 ml of the 20% zinc oxide ointment was mixed with K-Y Lubricating Jelly to reduce the viscosity of the ointment. The mixture was tested during intercourse. Other than being rather sticky and viscous, it did not cause any irritation.

Since zinc acetate is highly soluble in water, has a low pK value (high ionic dissociation), and causes no irritation, it was selected and used for subsequent testing to evaluate its ability to reduce HIV infectivity.

Example 2: Inhibition of HIV Virus by Zinc Acetate

In a series of tests done in the laboratories of Cambridge Biotech, Inc. (Rockville, Md.; this company was subsequently renamed as Biotech Research Labs, Inc.), the HIV-1 viral isolate was pre-treated with zinc acetate (ZnAc) before being contacted with an HIV-susceptible lymphocyte line designated as the H9 cell line (isolated at the National Institutes of Health, Bethesda, Md.). The pretreatment was done as follows.

20 mg of ZnAc powder was mixed in 1 ml RPMI cell culture medium (Whittaker Corp.). This 2% (w/v) salt mixture contained 7 mg/ml elemental Zn. Although ZnAc is highly soluble in water, it generated a precipitate in the culture medium, which contains protein. Therefore, a small quantity of HCl was added until the mixture became clear; the pH was about 5.5. The Zn concentration was reduced by half (and the pH was raised somewhat) when an equal volume (1 ml) of cell-free HIV-1 stock was added. The zinc/virus mixture was stirred and incubated for 2 hours at 37° C.

Following this first incubation step, the zinc/virus mixtures were diluted at 1:10, 1:30, and 1:100 ratios using culture medium, and aliquots were added to equal volumes of culture media containing H-9 lymphocytes that had been pretreated overnight with 2 ug/ml Polybreen. The lymphocyte mixtures were incubated for three hours at 37° C.; zinc concentrations during this step were 180, 60, and 18 ug/ml for the 1:10, 1:30, and 1:100 dilutions.

The cell aliquots were then washed twice, using culture medium, to remove free p24 proteins that are present in the initial viral stock. Such proteins will skew ELISA readings if not removed by washing. Cells were then resuspended in fresh medium containing 10% fetal calf serum (FCS) and cultured for 20 days. During this period, each tube was periodically sampled by hand-mixing the tube, withdrawing 100 ul of liquid from the top, and testing the sample for p24 antigens using ELISA assays.

The 1:10 dilutions, which contained 180 ug/ml Zn during the 3-hour incubation prior to washing, caused substantial mortality to the lymphocytes, and resulting ELISA data were discarded.

Based on visual observations, 1:30 dilutions (60 ug/ml Zn) retarded cell growth during the first few days; however, any such effect disappeared within a few days and the cells grew well during the rest of the assay period.

A positive control was used at each dilution. Viral aliquots not treated with zinc were identically diluted, mixed with lymphocytes, cultured, and tested. Negative controls were also run, in which H-9 cells were plated and grown in the absence of any virus or zinc; these provided background levels that vary slightly from day to day, depending on factors such as spectrophotometer calibrations and rinsing conditions.

Optical density (OD) data from the 1:30 dilution test are shown in FIG. 1. These quantities are averages based on triplicate samples. The p24 concentrations were indistinguishable from background levels, which indicates that the zinc treatment completely abolished viral infectivity.

Data from the 1:100 dilution test are shown in FIG. 2. One of the tubes became infected by mold after the 10th day, so subsequent values are based on averages from two samples. These results indicated that the zinc suppressed and retarded HIV infectivity; however, apparently, some small fraction of the viruses apparently remained infective.

Example 3: Diluted HIV Infectivity Tests

The tests described above, in Example 2, used an undiluted high-titer viral stock, which contained at least ten million infectious viral particles per ml. That concentration can be achieved in a laboratory only by special culturing, purification, and concentration techniques, and it is vastly higher than would actually occur in the ejaculate of an HIV-infected person (especially someone who is not in the end stages of the disease, and who might pose a significant risk of transmitting the virus to an uninfected sexual partner).

In subsequent tests, ZnAc was tested against diluted viral stocks and completely abolished the infectivity of the infected viruses. These tests used serial dilutions of the viral stocks, at ranges up to 1:10,000. To create the 1:10 dilution, 500 ul of viral stock was mixed with 4.5 ml of RPMI medium. Subsequent dilutions added 9 ml of RPMI medium to 1 ml from the preceding dilution.

A 2 ml aliquot from each dilution was mixed with an equal volume of 3% ZnAc dissolved in sterile distilled water; after mixing, the zinc concentration was 5.3 mg/ml Zn. These mixtures were incubated for 2 hours, then diluted with culture medium at 1:30, 1:100, and 1:1000 to reduce the toxicity of the zinc to lymphocytes. Four ml of lymphocytes were mixed with 4 ml of each zinc/virus mixture. The zinc/virus/cell mixtures were incubated at 37° C. for 3 hours; zinc concentrations were 88, 27, and 2.7 ug/ml in the 30, 100, and 1000 dilutions. During subsequent culturing, significant cell mortality was observed in the 88 ug/ml treatment batch, but no cell mortality was observed at the lower levels.

Following the 3 hour incubation, the cells were washed twice in RPMI medium and resuspended in fresh medium containing 10% FCS. Each solution was inoculated (2 ml; estimated minimum $2 \times 10^5$ cells per well) into each of three wells in a 12-well plate and cultured for 27 days, with periodic sampling and measuring of p24 antigens.

ELISA data for the 10x, 100x, and 1000x high-titer viral stock dilutions, treated with the 1000x dilution of the zinc/virus mixture (2.7 ug/ml Zn final concentration) are shown in FIG. 3. As shown, the zinc treatment completely blocked infectivity. Data for the diluted viral stocks treated with 1:100 zinc/virus dilutions (27 ug/ml Zn) were virtually identical; viral infectivity was completely blocked in those tests as well.

Negative controls were identically diluted cells that did not contain zinc or HIV. Positive controls which used 1:1000 dilutions of viral stock mixed with zinc-free RPMI were consistently highly infectious, even though their concentrations were 100x lower than the 1:10 mixtures in which infectivity was eliminated by zinc treatment. Other positive controls were tested at up to 100,000x dilutions; these were highly infective in two out of the three plates tested.

Figure 4:
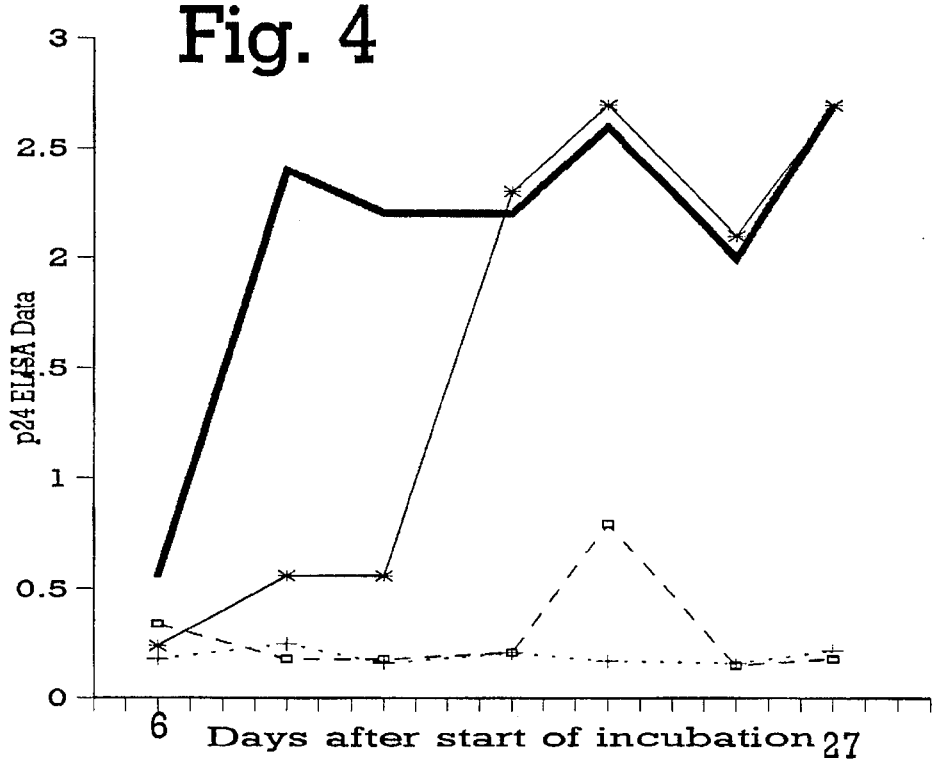
FIG. 4 shows that HIV infectivity was either eliminated or suppressed when high-titer viral stocks were incubated with varyious concentrations of zinc acetate.

While carrying out the viral dilution tests, tests were also performed using 2 ml of 3% ZnAc solution in distilled water mixed with 2 ml aliquots of undiluted viral stock. The zinc/virus mixtures were incubated for 2 hours, diluted with RPMI at 1:100 and 1:1000 ratios, and mixed with lymphocytes for three hours; zinc concentrations were 27 and 2.7 ug/ml. The cells were washed twice, inoculated into 12 well plates as described above, and cultured for 27 days. ELISA results are shown in FIG. 4. As shown, the 1:100 dilution (27 ug/ml Zn) completely prevented infectivity, while the 1:1000 dilution (2.7 ug/ml) delayed the onset of infection.

Example 4: HIV Precipitation Tests

Precipitation tests were also performed, using 2% ZnAc which was mixed with an equal volume of undiluted viral stock, incubated for 24 hours, and centrifuged at 1500 rpm in a tabletop centrifuge for 5 minutes. The supernatant was sampled (100 ul) and serially diluted by medium, at 1:10 followed by 2x dilutions (1:20, 1:40, 1:80, etc) to a maximum dilution of 1:10240. Each dilution was analyzed spectrophotometrically to determine the concentration of viruses suspended in solution. After sampling, each tube was hand-mixed and incubated for 24 hours. The solution near the top of the tube was sampled again, serially diluted, and tested using the ELISA assay. The tube was hand-mixed again, incubated for three more days, and sampled again to obtain Day 5 values.

The values for zinc-treated viruses averaged about 40% less than values for identically diluted solutions that did not receive zinc treatment. This indicates that the zinc caused substantial precipitation of the virus and lowered the concentration of free HIV particles in solution.

Thus, there has been shown and described a new and useful method of reducing the risk of sexual transmission of HIV. Although this invention has been exemplified for purposes of description and illustration by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by this invention.

REFERENCES

Agren, M. S., "Studies on zinc in wound healing," *Acta Dermato-Venereology*, Supplement 154: 1–36 (1990)

Alexander, N., et al, eds., *Heterosexual Transmission of AIDS*, (Wiley-Liss, New York, 1990)

Asculai, S. S., et al, "Inactivation of herpes simplex viruses by nonionic surfactants," *Antimicrob. Agents Chemother.* 13: 686–690 (1978)

Averette, H. E., et al, "Autoradiographic analysis of cell proliferation kinetics in human genital tissue," *Amer. J. Obstet. Gynec.* 108: 8–17 (1970)

Bach, J. F., "The multi-faceted zinc dependency of the immune system," *Immunology Today*: 225–227 (Nov. 1981)

Becher, P., *Emulsions: Theory and Practice*, 2nd ed., Amer. Chem. Soc. Monograph #162 (Reinhold Publ., New York, 1965)

Beller, F. K., and Schumacher, G. F. B., eds., *Biology of the Fluids of the Female Genital Tract* (Elsevier, New York, 1979)

Bracha, M. and M. J. Schlesinger, "Inhibition of Sindbis virus replication by zinc ions," *Virology* 72: 272–277 (1976)

Brawner, T. A., et al, "A Combined Chemical-Physical Treatment for Herpes Simplex Lesions in Guinea Pigs," *Arch. Dermatol. Res.* 265: 71–77 (1979)

Bray, T. M. and Bettger, W. J., "The physiological role of zinc as an antioxidant," *Free Radic. Biol. Med.* 8: 281–91 (1990)

Brody, I., "Topical treatment of recurrent herpes simplex ... zinc sulphate solution," *Brit. J. Dermatol.* 104: 191–194 (1981)

Butterworth, B. E. and Korant, B. D., *J. Virol.* 14: 282 (1975)

Calesnick, B. and Dinan, A. M., "Zinc deficiency and zinc toxicity," *Amer. Fam. Phys.* 37: 267–270 (1988)

Cannan, R. K., and Kibrick, A., "Complex formation between carboxylic acids and divalent metal cations," *J. Amer. Chem. Soc.* 60: 2314 (1938)

Chvapil, M., "New aspects in the biological role of zinc: a stabilizer of macromolecules and biological membranes," *Life Sciences* 13: 1041–1049 (1973)

Chvapil, M., "Effects of zinc on cells and biomembranes," *Med. Clin. North Amer.* 60: 799–812 (1976)

Chvapil, M., et al, "Reaction of vaginal tissue of rabbit and of cheek pouch of hamster to inserted collagen sponges treated with either zinc or copper," *Am. J. Obstet. Gynecol.* 130: 63–70 (1978)

Chvapil, M., et al, "Preliminary testing of the contraceptive collagen sponge," *Obstet. and Gynecol.* 56: 503–506 (1980)

Cohen, P. T., et al, eds., *The AIDS Knowledge Base* (Massachusetts Medical Society, Waltham, Mass. 1990)

Cousins, R. J., "Systemic transport of zinc," pp. 78–93 in Mills, C. F., ed., *Zinc in Human Biology* (Springer-Verlag, New York, 1989)

Crowe, S., et al, "Antiviral drug therapy for HIV infection: Rationale," section 3.2.5 in Cohen et al 1990

Eby, G. A., and W. W. Halcomb, "Use of topical zinc to prevent recurrent herpes simplex infection: review of literature and suggested protocols," *Medical Hypotheses* 17: 157–165 (1985)

Eliasson, R. and Lindholmer, C., "Zinc in human seminal plasma," *Andrology* 3: 147 (1971)

Eliasson, R., "Effect of zinc on human sperm respiration," *Life Science* 10: 1317 (1971)

Fabris, N., et al, "AIDS zinc deficiency, and thymic hormone failure," *JAMA* 259: 839–849 (1988)

Fahim, M., et al, "New treatment for herpes simplex virus type 2: female patients," *J. Medicine* 11(2&3): 143–167 (1980a)

Fahim, M. S. and Brawner, T. A., "Treatment of genital herpes simplex virus in male patients," *Arch. Andrology* 4: 79–85 (1980b)

Fair, W. R., et al, "Prostatic antibacterial factor, identity and significance," *Urology* 7: 169–177 (1976)

Ferenczy, A. and Guralnick, M. S., "Morphology of the human vagina," pp. 3–12 in Beller and Schumacher 1979

Firpo, E. J., and Palma, E. L., "Inhibition of foot and mouth disease virus and procapsid synthesis by zinc ions," Arch. Virol. 61: 175–181 (1979)

Fosmire, G. J., "Zinc toxicity," Amer. J. Clin. Nutr. 51: 225–227 (1990)

Fridlender, B., et al, "Selective inhibition of herpes simplex virus type 1 DNA polymerase by zinc ions," Virology 84: 551–554 (1978)

Gennaro, A. R., ed., Remington's Pharmaceutical Sciences, 18th Edition (Mack Publ., Easton, Pa. 1990)

Godfrey, J. C., et al, Letters to the Editor, Antimicrobial Agents and Chemotherapy 32: 605–609 (1988)

Gordon, Y. J., et al, "Irreversible inhibition of herpes simplex virus replication in BSC-1 cells by zinc ions," Antimicrob. Agents Chemother. 8: 377–380 (1975)

Gottlieb, M. S., et al, eds. Current Topics in AIDS: Volume 2 Wiley & Sons, NY, 1989

Gupta, P. and Rapp, F., "Effect of zinc ions on synthesis of herpes simplex virus type 2-induced polypeptides," Proc. Soc. Exp. Biol. and Med. 152: 455–458 (1976)

Hedberg, K. K., et al, "Phorbol ester-induced actin cytoskeletal reorganization requires a heavy metal ion," Cell Regul. 2: 1067–79 (1991)

Hennig, B. et al, "Zinc deficiency alters barrier function of cultured porcine endothelial cells," J. Nutr. 122: 1242–7 (1992)

Ho, D. D., et al, "Infrequency of isolation of HTLV-III virus from saliva in AIDS," New Engl. J. Med. 313: 606 (1985)

Holmberg, S. D., et al, "Prior herpes simplex virus type 2 infection as a risk factor for HIV infection," J. Amer. Med. Assn. 259: 1048–50 (1988)

Homonnai, Z. T., et al, "Prolactin and zinc in the human ejaculate," Andrologia 10: 66 (1978)

Kaszuba, M. and Hunt, G. R., "Protection against membrane damage: an investigation of the effects of $Zn^{++}$ and $Ca^{++}$," J. Inorg. Biochem. 40: 217–25 (1990)

Kono, R., and Nakajima, A., eds., Herpes Viruses and Virus Chemotherapy: Pharmacological and Clinical Approaches (Excerpta Medica, N.Y., 1985)

Korant, B. D., et al, "Zinc ions inhibit replication of rhinoviruses," Nature 248: 588–590 (1974)

Korant, B. D. and B. E. Butterworth, "Inhibition by zinc of rhinovirus protein cleavage," J. Virol. 18: 298–306 (1976)

Kreiss, J., et al, "Efficacy of nonoxynol contraceptive sponge use in preventing heterosexual acquisition of HIV in Nairobi prostitutes," JAMA 268: 477–482 (1992)

Leonard, A., et al, "Mutagenicity, carcinogenicity and teratogenicity of zinc," Mutation Research 168: 343–353 (1986)

Levy, J. A., "The transmission of AIDS: The case of the infected cell," JAMA 259: 3037–3038 (1988)

Levy, J. A., ed., AIDS: Pathogenesis and Treatment (Marcel Dekker, New York, 1989)

Lide, D. R., ed., CRC Handbook of Chemistry and Physics, 71st Edition (Boca Raton, Fla., 1990)

Linke, W. F., ed., Solubility of Inorganic and Metal Organic Compounds, 4th Edition, 1965

Mahadevan, D., et al, "Protection against membrane-mediated cytotoxicity by calcium and zinc," Am. J. Pathol. 136: 513–20 (1990)

Marmar, J. L., "Values for zinc in whole semen, fractions of split ejaculate, and expressed prostatic fluid," Urology 16: 478–480 (1980)

Meftah, S., et al, "Ecto 5' nucleotidase as a sensitive indicator of human zinc deficiency," J. Lab. Clin. Med. 118: 309–316 (1991)

Mills, C. F., ed., Zinc in Human Biology (Springer-Verlag, New York, 1989)

Nardelli, J., et al, "Base sequence discrimination by zinc-finger DNA-binding domains," Nature 349: 175–178 (1991)

Pasternak, C. A., "Transmembrane communication and disease," Indian J. Biochem. Biophys. 27: 363–4 (1990)

Pasternak, C. A., et al, "Membrane damage: Common mechanisms of induction and prevention," FEMS Microbiol. Immunol. 5: 83–92 (1992)

Paz, G., "Human semen analysis," Int. J. Fertil. 22: 140 (1977)

Phillips, D. M. and Bourinbaiar, A. S., "Mechanism of HIV spread from lymphocytes to epithelia," Virology 186: 261–273 (1992)

Pearce-Pratt, R and Phillips, D. M., "Studies of adhesion of lymphocytic cells: Implications for sexual transmission of HIV," Biol. of Reproduction 48: 431–445 (1993)

Putney, S. D. and Bolognesi, D. P., eds, AIDS Vaccine Research and Clinical Trials (Marcel Dekker, New York, 1990)

Reichman, R. C., "Treatment of genital herpes simplex infections with topically administered antiviral drugs," pp. 149–154 in Kono and Nakajima 1985

Resnick, L., et al, "Anti-HIV Screening Technology," pp. 311–325 in Alexander et al 1990

Rice, W. G., et al, "Inhibition of HIV-1 infectivity by zinc-ejecting aromatic C-nitroso compounds," Nature 361: 473–475 (1993)

Robinson, J. R. and Lee, V. H., eds., Controlled Drug Delivery (Marcel Dekker, New York, 1987)

Sadhu, C. and Gedamu, L., "Metal specific posttranscriptional control of human metallothionein genes," Mol. Cell. Biol. 9: 5738–41 (1989)

St. Onge, D. and Gicquaud, C., "Research on the mechanism of interaction between actin and membrane lipids," Biochem. Biophys. Res. Commun. 167: 40–7 (1990)

Sergio, W., "Zinc salts that may be effective against the AIDS virus HIV," Medical Hypotheses 26(4): 251–253 (1988)

Sharma, R., et al, "Antiviral effect of zinc ions on aphthovirus in BHK-21 cell line," Acta Virol. 29: 517 (1985)

Shlomai, J., et al, "Effect of zinc ions on the synthesis of herpes simplex virus DNA in infected BSC-1 cells," Virology 66: 330–335 (1975)

Sillen, L. G., and Martell, A. E., Stability Constants of Metal Ion Complexes, Special Publication No. 25 (The Chemical Society, London, 1971)

Sillen, L. G., and Martell, A. E., Stability Constants of Metal Ion Complexes, Special Publication No. 17 (The Chemical Society, London, 1964)

Starcich, B. R., et al, "Identification and characterization of conserved and variable regions in the envelope gene of HTLV-III/LAV, the retrovirus of AIDS," Cell 45: 637–648 (1986)

Tennican, P., et al, "Topical zinc in the treatment of mice infected intravaginally with herpes genitalis virus," Proc. Soc. Exp. Biol. Med. 164: 593–597 (1980)

Tennican, P. O., et al, "The diverse effects of topical and systemic administration of zinc on the virulence of herpes simplex genitalis," *Life Sciences* 24: 1877–1884 (1979).

Vallee, B. I., "Zinc: biochemistry, physiology, toxicology and clinical pathology," *Biofactors* 1(1): 31–36 (1988)

Vallee, B. I. and Falchuk, K. H., "The biochemical basis of zinc physiology," *Physiological Reviews* 73: 79–118 (1993)

Wahba, A., "Topical application of zinc solutions: A new treatment for herpes simplex infections of the skin?" *Acta Derm. Venerol. (Stockholm)* 60: 175–177 (1980)

Weber, J. N. and Weiss, R. A., "HIV infection: The cellular picture," *Scientific American*, pp. 101–109 (October 1988)

Weiner, R. G., "AIDS and zinc deficiency," *JAMA* 252: 1409–1410 (1984)

Weislow, O. S., et al, "New soluble formazan assay for HIV-1 cytopathic effects," *J. Natl. Cancer Inst.* 81: 577–586 (1989)

Williams, W. L., "New antifertility agents active in the rabbit vaginal contraception method," *Contraception* 22: 659–672 (1980)

Zacharopoulos, V. A., et al, "Lymphocyte-facilitated infection of epithelia by Human T-cell Lymphotropic Virus Type I," *J. Virology* 66: 4601–4605 (1992)

Zalewski, P. D., "Regulation of protein kinase C by zinc-dependent interaction with actin," *Biochem. Int* 24: 1103–10 (1991).

Zaslavsky, V., "Inhibition of vaccinia virus growth by zinc ions: effects on early RNA and thymidine kinase synthesis," *J. Virology* 29: 405–408 (1979)

I claim:

1. A method of reducing the risk of sexual transmission of human immunodeficiency virus, comprising spreading a topical genital lubricant across genital surfaces that come into intimate contact with a sexual partner during intercourse, wherein the topical genital lubricant contains at least one water-soluble organic zinc salt that releases zinc ions in solution, and wherein the topical genital lubricant does not irritate the genital surfaces or cause other adverse effects, and wherein the zinc salt is present in the topical genital lubricant at a concentration that can reduce infectivity of mature HIV particles when mixed with such viral particles in aqueous solution and incubated for two hours at 37° C., and wherein the genital lubricant is characterized by the absence of any deleterious compound at a concentration that would generate a significant adverse effect if applied to genital surfaces and used repeatedly during numerous acts of sexual intercourse.

2. The method of claim 1, wherein the topically active anti-viral agent comprises a carboxylic acid salt of zinc.

3. The method of claim 2 wherein the carboxylic acid salt of zinc is selected from the group consisting of zinc acetate, zinc propionate, zinc butyrate, zinc formate, zinc glycerate, zinc glycolate, zinc lactate, and zinc gluconate.

\* \* \* \* \*